(12) United States Patent
Koshijima et al.

(10) Patent No.: US 10,596,045 B2
(45) Date of Patent: Mar. 24, 2020

(54) COMPOSITE STRETCHABLE MEMBER, WEARABLE ARTICLE, AND METHOD FOR PRODUCING WEARABLE ARTICLE

(71) Applicant: ZUIKO CORPORATION, Osaka (JP)

(72) Inventors: Miwa Koshijima, Osaka (JP); Hideyuki Nakamura, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 127 days.

(21) Appl. No.: 15/736,103

(22) PCT Filed: Jun. 17, 2016

(86) PCT No.: PCT/JP2016/068158
§ 371 (c)(1),
(2) Date: Dec. 13, 2017

(87) PCT Pub. No.: WO2016/208513
PCT Pub. Date: Dec. 29, 2016

(65) Prior Publication Data
US 2018/0140473 A1    May 24, 2018

(30) Foreign Application Priority Data
Jun. 22, 2015  (JP) .................................. 2015-124927

(51) Int. Cl.
*A61F 13/15*    (2006.01)
*B32B 5/08*    (2006.01)
(Continued)

(52) U.S. Cl.
CPC .. *A61F 13/15804* (2013.01); *A61F 13/15593* (2013.01); *A61F 13/15699* (2013.01);
(Continued)

(58) Field of Classification Search
CPC ... B29C 66/71; B29C 65/086; B29C 66/1122; B29C 66/221; B29C 66/234;
(Continued)

(56) References Cited

U.S. PATENT DOCUMENTS

2004/0133180 A1  7/2004  Mori et al.
2006/0270302 A1  11/2006  Ando et al.
(Continued)

FOREIGN PATENT DOCUMENTS

CN    101410080    4/2009
EP    1 997 463    12/2008
(Continued)

OTHER PUBLICATIONS

International Search Report dated Sep. 13, 2016 in International (PCT) Application No. PCT/JP2016/068158.
(Continued)

*Primary Examiner* — Arti Singh-Pandey
(74) *Attorney, Agent, or Firm* — Wenderoth, Lind & Ponack, L.L.P.

(57) ABSTRACT

Providing two sheets which are opposed to each other, and a plurality of elastic elements each disposed between the sheets to extend along a stretchable direction of a composite stretchable member in such a manner as to be stretchable in the stretchable direction, wherein: the sheets are bonded together in a plurality of bonding sections, wherein each of the bonding sections is configured to continuously extend along a line intersecting the stretchable direction and to intersect the plurality of elastic elements; and each of the elastic elements is bonded to the sheets at intersection points with the bonding sections.

15 Claims, 21 Drawing Sheets

(51) Int. Cl.
    *B29C 65/00* (2006.01)
    *B29C 65/08* (2006.01)
    *A61F 13/49* (2006.01)
    *B29D 99/00* (2010.01)
    *B29L 31/48* (2006.01)

(52) U.S. Cl.
    CPC .. *A61F 13/15739* (2013.01); *A61F 13/15747* (2013.01); *A61F 13/4902* (2013.01); *A61F 13/49011* (2013.01); *B29C 65/086* (2013.01); *B29C 66/1122* (2013.01); *B29C 66/43* (2013.01); *B29C 66/7294* (2013.01); *B29C 66/81433* (2013.01); *B29C 66/83411* (2013.01); *B29D 99/0064* (2013.01); *B32B 5/08* (2013.01); *A61F 2013/49025* (2013.01); *B29C 66/221* (2013.01); *B29C 66/234* (2013.01); *B29C 66/431* (2013.01); *B29C 66/433* (2013.01); *B29C 66/71* (2013.01); *B29K 2995/0046* (2013.01); *B29L 2031/4878* (2013.01)

(58) Field of Classification Search
    CPC ..... B29C 66/43; B29C 66/431; B29C 66/433; B29C 66/7294; B29C 66/81433; B29C 66/83411; B29K 2075/00; B29K 2995/0046; A61F 13/15593; A61F 13/15699; A61F 13/15739; A61F 13/15747; A61F 13/15804; A61F 13/49011; A61F 13/4902; A61F 2013/49025; B29D 99/0064; B29L 2031/4878; B32B 5/08
    See application file for complete search history.

(56) References Cited

U.S. PATENT DOCUMENTS

| | | |
|---|---|---|
| 2008/0300565 A1 | 12/2008 | Takahashi et al. |
| 2010/0076394 A1 | 3/2010 | Hayase et al. |
| 2010/0190405 A1 | 7/2010 | Takebe et al. |
| 2011/0284157 A1 | 11/2011 | Takahashi et al. |
| 2015/0064387 A1 | 3/2015 | Imai et al. |
| 2016/0067115 A1 | 3/2016 | Ishikawa et al. |
| 2016/0100990 A1 | 4/2016 | Fujita et al. |
| 2017/0051444 A1 | 2/2017 | Takebe et al. |

FOREIGN PATENT DOCUMENTS

| | | |
|---|---|---|
| EP | 2 161 360 | 3/2010 |
| EP | 2 813 347 | 12/2014 |
| JP | 7-252762 | 10/1995 |
| JP | 2002-273808 | 9/2002 |
| JP | 2008-55198 | 3/2008 |
| JP | 2008-161514 | 7/2008 |
| JP | 4322140 | 6/2009 |
| WO | 2014/103464 | 7/2014 |
| WO | 2014/156949 | 10/2014 |
| WO | 2014/200104 | 12/2014 |
| WO | 2016/121975 | 8/2016 |

OTHER PUBLICATIONS

Extended European Search Report dated Feb. 8, 2018 in European Patent Application No. 16814284.2.
Notification of Reasons for Refusal dated Apr. 11, 2019 in Japanese Application No. 2017-524870, with English translation.
Notice of Reasons for Refusal dated Sep. 10, 2019 in Japanese Patent Application No. 2017-524870, with English Translation.

STAGE 1

STAGE 2

STAGE 3

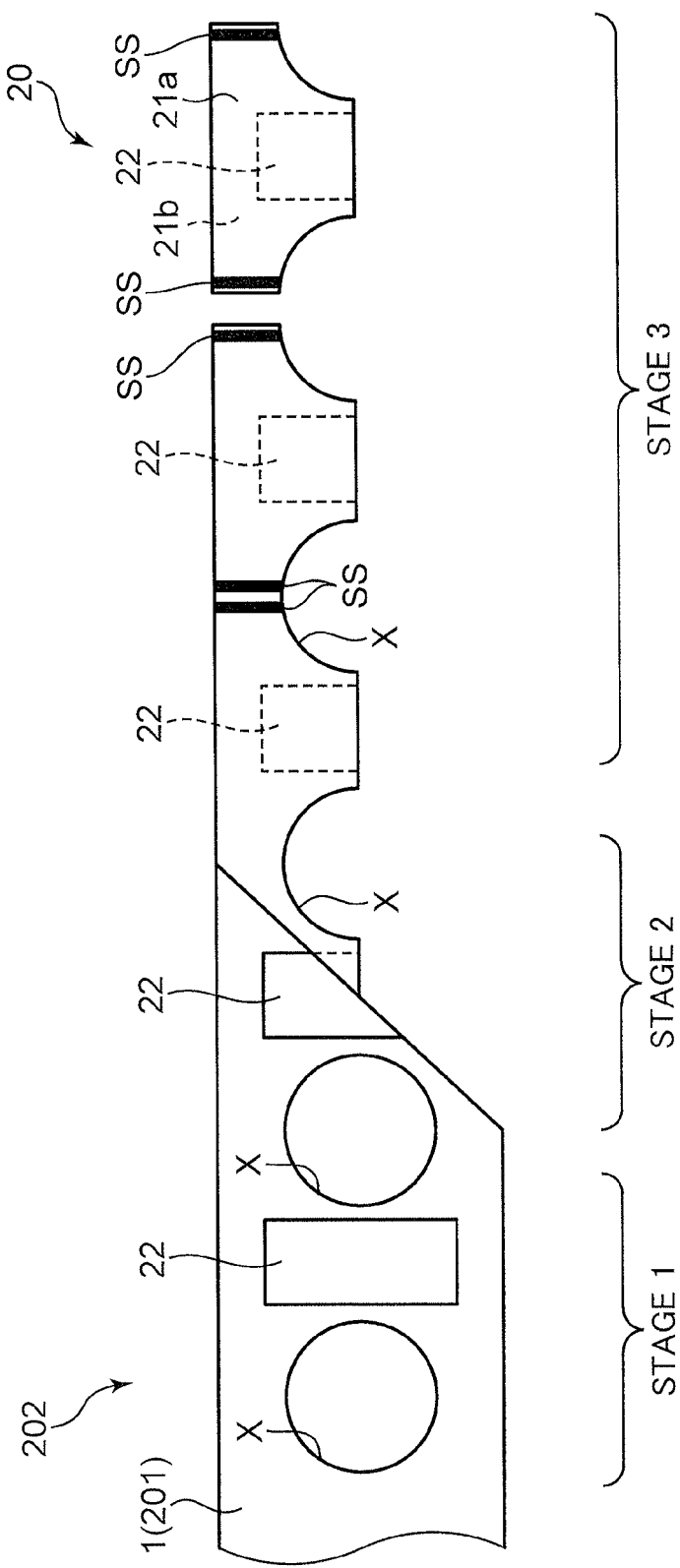

COMPOSITE STRETCHABLE MEMBER, WEARABLE ARTICLE, AND METHOD FOR PRODUCING WEARABLE ARTICLE

TECHNICAL FIELD

The present invention relates to a composite stretchable member, a wearable article, and a production method for a wearable article.

BACKGROUND ART

Heretofore, there has been known a wearable article such as a disposable diaper having a waist portion and a crotch portion. In this type of wearable article, with a view to providing good wearing comfort or the like, the waist portion of the wearable article is composed of a composite stretchable member capable of being stretched and restored, in some cases.

As the composite stretchable member, there has been known a composite stretchable member described, for example, in the following Patent Literature 1.

The member described in the Patent Literature 1 comprises two sheets and a plurality of elastic elements, wherein, by bonding these sheets together, the elastic elements are fixed between the sheets. In this member, the two sheets, or associated ones of the sheets and the elastic elements, are intermittently bonded together, in a longitudinal direction of the sheet and a direction orthogonal to the longitudinal direction.

In the member described in the Patent Literature 1, particularly in a direction intersecting the longitudinal direction of the sheet, i.e., in a direction intersecting a stretchable direction of the member, the two sheets are bonded together just intermittently. This can cause difficulty in ensuring enough bonding force between the two sheets, leading to a problem such as debonding between the two sheets. For example, assume that this member is used as a waist portion of a wearable article in a state in which the stretchable direction of the member is coincident with a waist circumferential direction. In this case, there is a possibility of occurrence of a problem that the two sheets are debonded from each other when the waist region is pulled up and down during attaching and removing of the wearable article.

CITATION LIST

Parent Document

Patent Literature 1: JP 4322140 B

SUMMARY OF INVENTION

It is an object of the present invention to provide a composite stretchable member capable of further increasing a bonding force between two sheets thereof, a wearable article using the composite stretchable member, and a production method for the wearable article.

In order to solve the above problem, the present invention provides a composite stretchable member which is stretchable in a specific direction. The composite stretchable member comprises two sheets which are opposed to each other, and a plurality of elastic elements each disposed between the sheets to extend along the specific direction in such a manner as to be stretchable in the specific direction, wherein: the sheets are bonded together in a plurality of bonding sections, wherein each of the bonding sections is configured to continuously extend along a line intersecting the specific direction and to intersect the plurality of elastic elements; and each of the elastic elements is bonded to the sheets at intersection points with the bonding sections.

The present invention also provides a wearable article comprising a waist portion to be disposed around a waist region of a wearer, wherein at least part of the waist portion is formed of the composite stretchable member configured as above.

The present invention further provides a method of producing a wearable article, wherein the wearable article comprises a waist portion to be disposed around a waist region of a wearer and a crotch portion to be disposed in a crotch region of the wearer. The method comprises: a bonded body forming step of, after providing a continuous body of the composite stretchable member configured as above, conveying the continuous body in a longitudinal direction thereof so as to form the waist portion, and bonding the crotch portion to the continuous body, such that a longitudinal direction of the crotch portion is oriented orthogonal to the longitudinal direction of the continuous body to thereby form a bonded body; a double-folding step of double-folding the bonded body along a folding line defined by a center line of the bonded body in a width direction orthogonal to the longitudinal direction of the continuous body; a side sealing step of mutually bonding superimposed portions of the continuous body at an intermediate position between adjacent ones of a series of the crotch portions in the longitudinal direction of the continuous body, along a direction orthogonal to the longitudinal direction of the continuous body, to thereby form a side seal; and a cutting step of cutting the continuous body along a cutting line in the side seal.

The present invention makes it possible to further increase a bonding force between associated ones of the elastic elements and the sheets.

BRIEF DESCRIPTION OF DRAWINGS

FIG. 21 is a diagram for explaining another example of the production method for the disposable diaper depicted in FIG. 15.

DESCRIPTION OF EMBODIMENTS

With reference to the accompanying drawings, the present invention will now be described based on embodiments thereof. It should be noted that the following embodiments will be shown and described as specific example of the present invention, but are not meant to limit the technical scope of the present invention set forth in the appended claims.

(1) Configuration of Composite Stretchable Member

Figure 1:
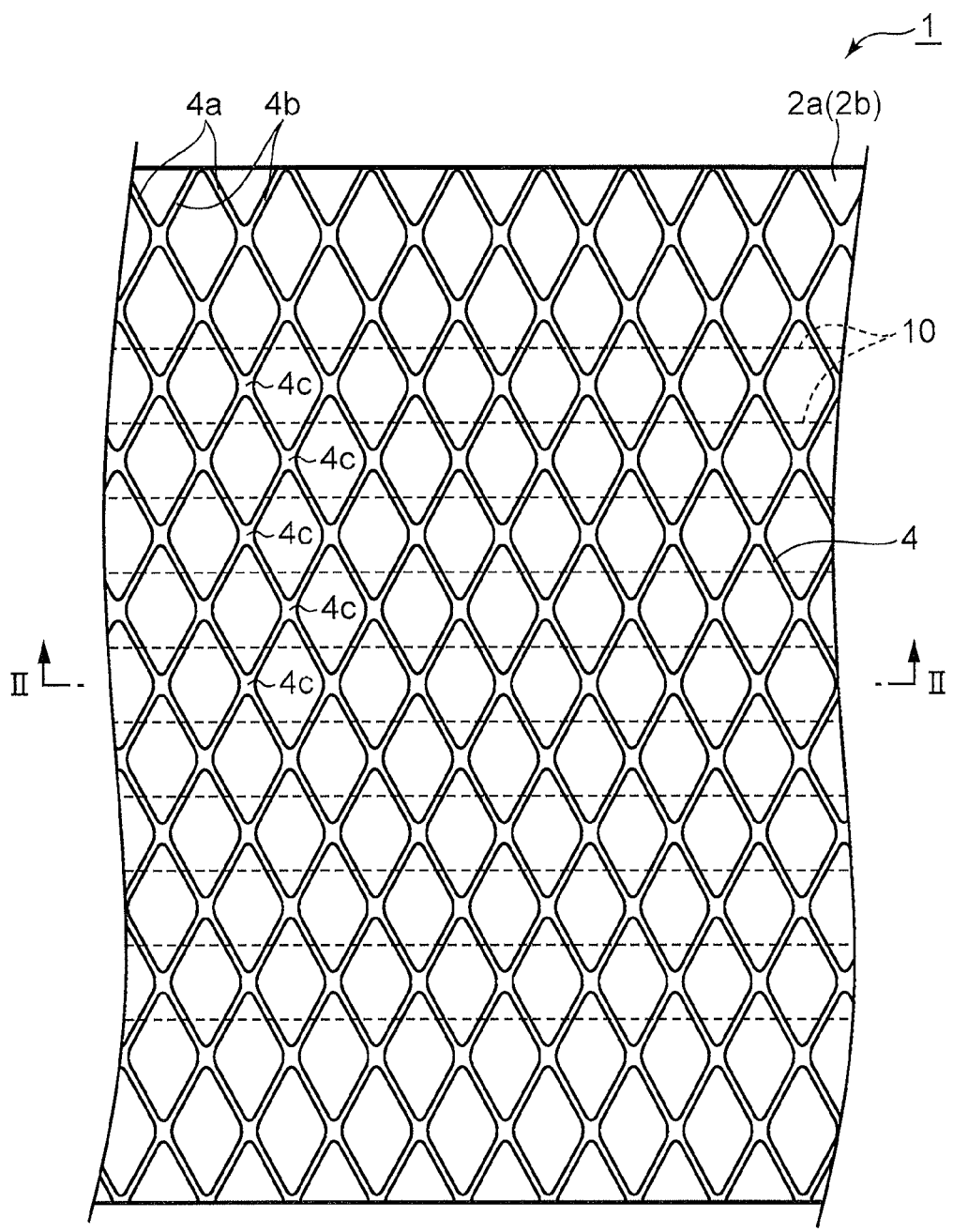
FIG. 1 is a plan view of a composite stretchable member according to one embodiment of the present invention.
Figure 2:
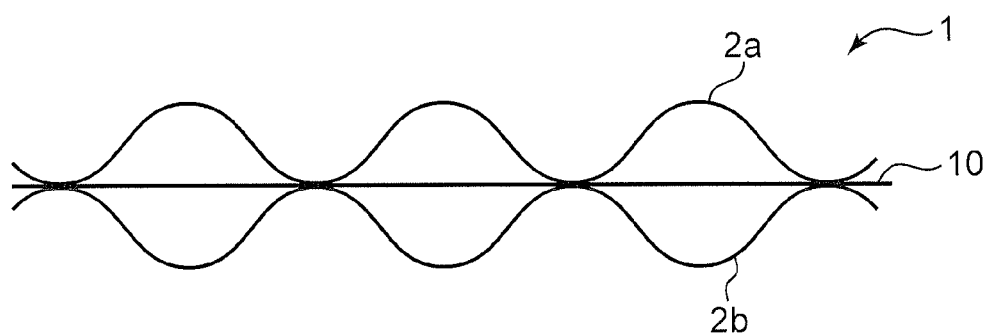
FIG. 2 is part of a sectional view taken along the line 1141 in FIG. 1.

FIG. 1 is a plan view of a composite stretchable member according to one embodiment of the present invention. FIG. 2 is part of a sectional view taken along the line II-II in FIG. 1.

The composite stretchable member 1 comprises two long sheets 2a, 2b which are opposed to each other, and a plurality of long elastic elements 10 which are stretchable in a longitudinal direction thereof. Each of the elastic elements 10 is disposed between the two sheets 2a, 2b to extend along the longitudinal direction of the sheets 2a, 2b (a specific direction, a rightward-leftward direction in FIG. 1), in such a manner as to be stretchable in the longitudinal direction, i.e., so as to be stretched and restored in the longitudinal direction. In this embodiment, these elastic elements 10 are arranged at equal intervals (equally spaced-apart relation to each other) in a width direction of the sheets 2a, 2b (a direction orthogonal to the longitudinal direction of the sheets 2a, 2b), to extend parallel to the longitudinal direction of the sheets 2a, 2b.

In this embodiment, non-woven fabric is used as a material for the sheets 2a, 2b.

Figure 3:
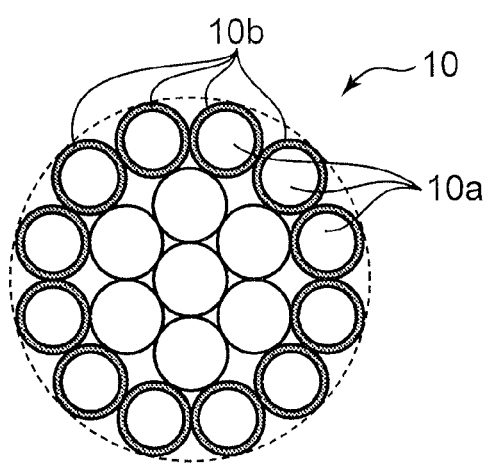
FIG. 3 is a schematic sectional view depicting a cross-section of an elastic element.

In this embodiment, as depicted in FIG. 3, each of the elastic elements 10 is formed using a multi-strand element in which a plurality of rubber strings (fibrous elastic bodies) 10a are assembled in the form of a bundle, wherein each of at least part of the rubber strings 10a has an outer periphery covered by a covering layer 10b. More specifically, among the plurality of rubber strings 10a, each of some rubber strings 10a disposed particularly in an outer periphery of the elastic elements is covered by the covering layer 10b. Alternatively, it is to be understood that each of the plurality of rubber strings 10a may be covered by the covering layer 10b.

Examples of a material for the rubber strings 10a include polyurethane. Examples of a material for the covering layer 10b include lubricant such as silicone oil, or magnesium stearate.

The two sheets 2a, 2b are bonded together, and further the elastic elements 10 is bonded to the sheets 2a, 2b, in lattice-patterned bonding sections 4, as depicted in FIG. 1.

Figure 4:
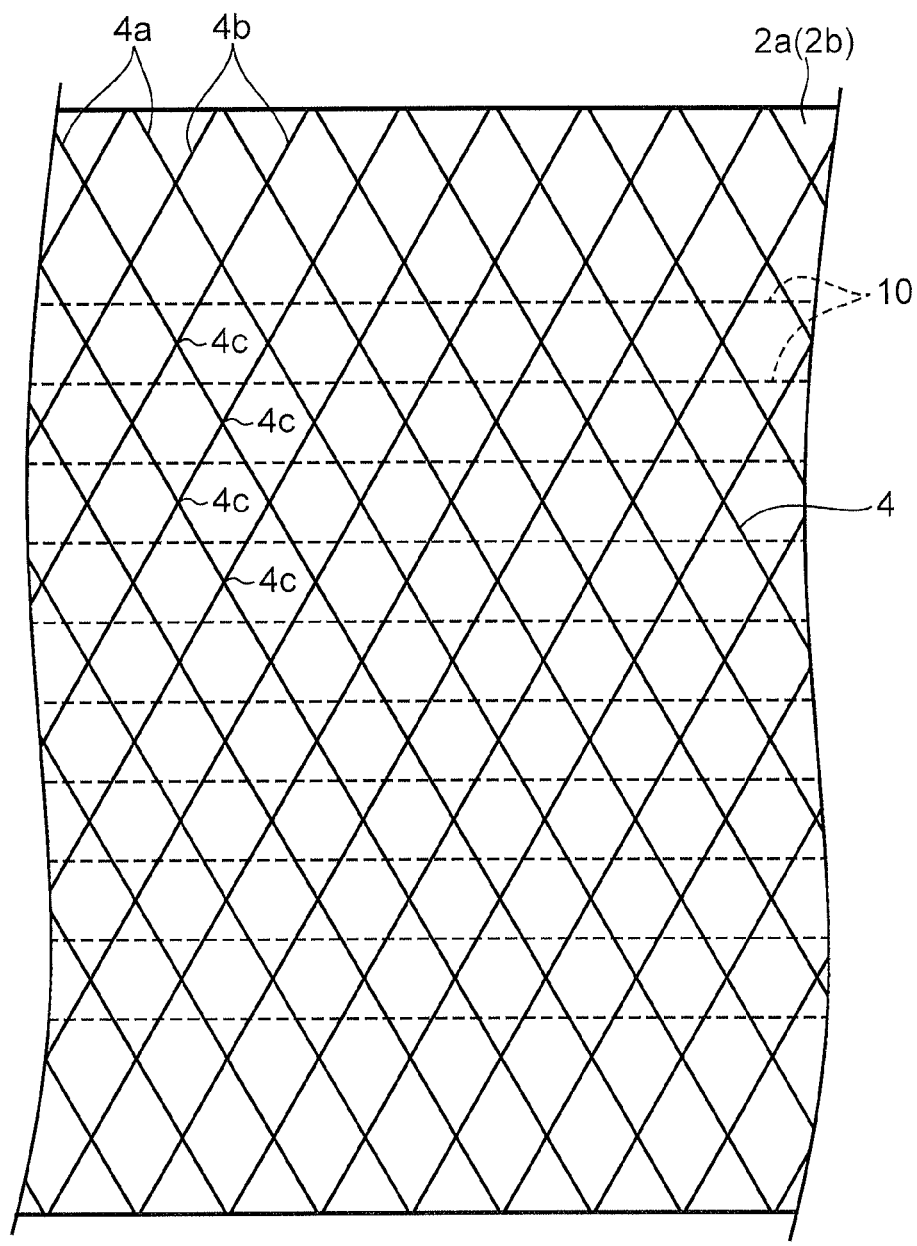
FIG. 4 is a view corresponding to FIG. 1 and schematically depicting bonding sections.

FIG. 4 is a view corresponding to FIG. 1 and schematically depicting the bonding sections. As depicted in FIGS. 1 and 4, the bonding sections 4 comprise a plurality of first bonding sections 4a, and a plurality of second bonding sections 4b.

The first bonding sections 4a are arranged at equal intervals in the longitudinal direction of the sheets 2a, 2b, to extend parallel to each other along the width direction of the sheets 2a, 2b.

The second bonding sections 4b are arranged at equal intervals in the longitudinal direction of the sheets 2a, 2b, to extend parallel to each other along the width direction of the sheets 2a, 2b. The second bonding sections 4b extend to intersect the first bonding sections 4a to thereby form the lattice-patterned bonding sections 4.

In this embodiment, each of the first bonding sections 4a and the second bonding sections 4b is inclined with respect to the width direction of the sheets 2a, 2b. Further, an angle of this inclination is set to be less than 45 degrees. For example, this inclination angle is set to 30 degrees.

Each of the first bonding sections 4a and the second bonding sections 4b has a symmetrical shape with respect to each of two straight lines extending in the longitudinal and width directions of the sheets 2a, 2b. The first bonding sections 4a and the second bonding sections 4b are arranged such that a spaced-apart distance between adjacent ones of the first bonding sections 4a is coincident with a spaced-apart distance between adjacent ones of the second bonding sections 4b. Accordingly, each of the bonding section 4 defines diamond shape whose two diagonal lines extend in the longitudinal and width directions of the sheets 2a, 2b. In particular, as mentioned above, each of the first bonding sections 4a and the second bonding sections 4b is inclined at an inclination angle of less than 45 degrees with respect to the width direction of the sheets 2a, 2b, and therefore each of the diamond shapes is defined to extend in the width direction. Intersection points 4c of the first bonding sections 4a with the second bonding sections 4b (hereinafter referred to occasionally as "bonding section-side intersection points") lie side-by-side at equal intervals on a straight line extending in the longitudinal direction of the sheets 2a, 2b, and also lie side-by-side at equal intervals on a straight line extending in the width direction of the sheets 2a, 2b.

Each of the bonding sections 4 (4a, 4b) intersects all of the elastic elements 10, and extends along a line intersecting a stretchable direction of the elastic elements 10. Specifically, each of the bonding sections 4 extends over between widthwise opposite regions of the sheets 2a, 2b outside a region in which the elastic elements 10 are arranged.

Each of the elastic elements 10 intersects the bonding sections 4, at positions other than the bonding section-side intersection points 4c, i.e., at positions spaced apart from the bonding section-side intersection points 4c, wherein the elastic element 10 is bonded to the sheets 2a, 2b at these positions.

This will be more specifically described with reference to FIG. 5 enlargedly depicting part of FIG. 1.

Figure 5:
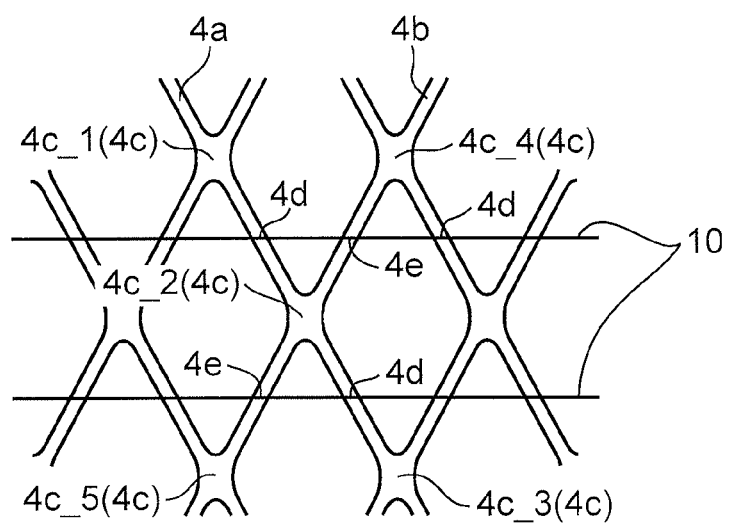
FIG. 5 is a view enlargedly depicting part of FIG. 1.

Each of the elastic elements 10 is disposed to pass, respectively, through positions between adjacent ones of the bonding section-side intersection points 4c on each of the first bonding sections 4a (e.g., pass, respectively, between the bonding section-side intersection point $4c\_1$ and the bonding section-side intersection point $4c\_2$, and between the bonding section-side intersection point $4c\_2$ and the bonding section-side intersection point $4c\_3$, depicted in FIG. 5). That is, a first elastic element-side intersection point 4d which is an intersection point of each of the elastic elements 10 with each of the first bonding sections 4a lies between adjacent ones of the bonding section-side intersection points 4c on the first bonding section 4a, and the elastic element 10 and the sheets 2a, 2b are bonded together at the position of this intersection point 4d.

Similarly, each of the elastic elements 10 is disposed to pass, respectively, through positions between adjacent ones of the bonding section-side intersection points 4c on the second bonding sections 4b (e.g., pass, respectively, between the bonding section-side intersection point 4c_4 and the bonding section-side intersection point 4c_2, and between the bonding section-side intersection point 4c_2 and the bonding section-side intersection point 4c_5, depicted in FIG. 5). That is, a second elastic element-side intersection point 4e which is an intersection point of each of the elastic elements 10 with each of the second bonding sections 4b lies between adjacent ones of the bonding section-side intersection points 4c on the second bonding sections 4b, and the elastic element 10 and the sheets 2a, 2b are bonded together at the position of this intersection point 4e.

In this embodiment, each of the elastic elements 10 is disposed to pass through a center between adjacent ones of the bonding section-side intersection points 4c on each of the first bonding sections 4a, and a center between adjacent ones of the bonding section-side intersection points 4c on each of the second bonding sections 4b, i.e., to intersect the first bonding section 4a and the second bonding section 4b at these centers, and bonded to the sheets 2a, 2b at these centers.

Accordingly, the first elastic element-side intersection point 4d and the second elastic element-side intersection point 4e alternately lie in a straight line extending in the width direction of the sheets 2a, 2b. Further, intersection points of the elastic elements 10 with the bonding sections 4, i.e., bonded points 4d, 4e of each of the elastic elements 10 to the sheets 2a, 2b, are arranged at equal intervals in the longitudinal direction of the sheets 2a, 2b.

In the bonding sections 4, the two sheets 2a, 2b are bonded together, and further each of the elastic elements 10 is bonded to the sheets 2a, 2b, by means of welding. In this embodiment, they are bonded together by means of ultrasonic welding.

The sheets 2a, 2b are partially melted, and welded to each other, so that they are bonded together. On the other hand, as to the elastic elements 10 and the sheets 2a, 2b, the part of the sheets 2a, 2b is partially melted, and the covering layers 10b in each of the elastic elements 10 are melted, so that each of the elastic elements 10 is welded to the sheets 2a, 2b.

Specifically, in this embodiment, the rubber strings 10a and the covering layers 10b are formed using rubber strings having a melting point of about 200° C. and magnesium stearate having a melting point of less than about 200° C. (of about 120° C.), respectively. Thus, during welding of each of the elastic elements 10 to the sheets 2a, 2b, the covering layers 10b are melted without causing melting of the rubber strings 10a, and welded to the sheets 2a, 2b.

(2) Production Apparatus for Composite Stretchable Member

Next, a production apparatus for producing the above composite stretchable member 1 will be described.

Figure 6:
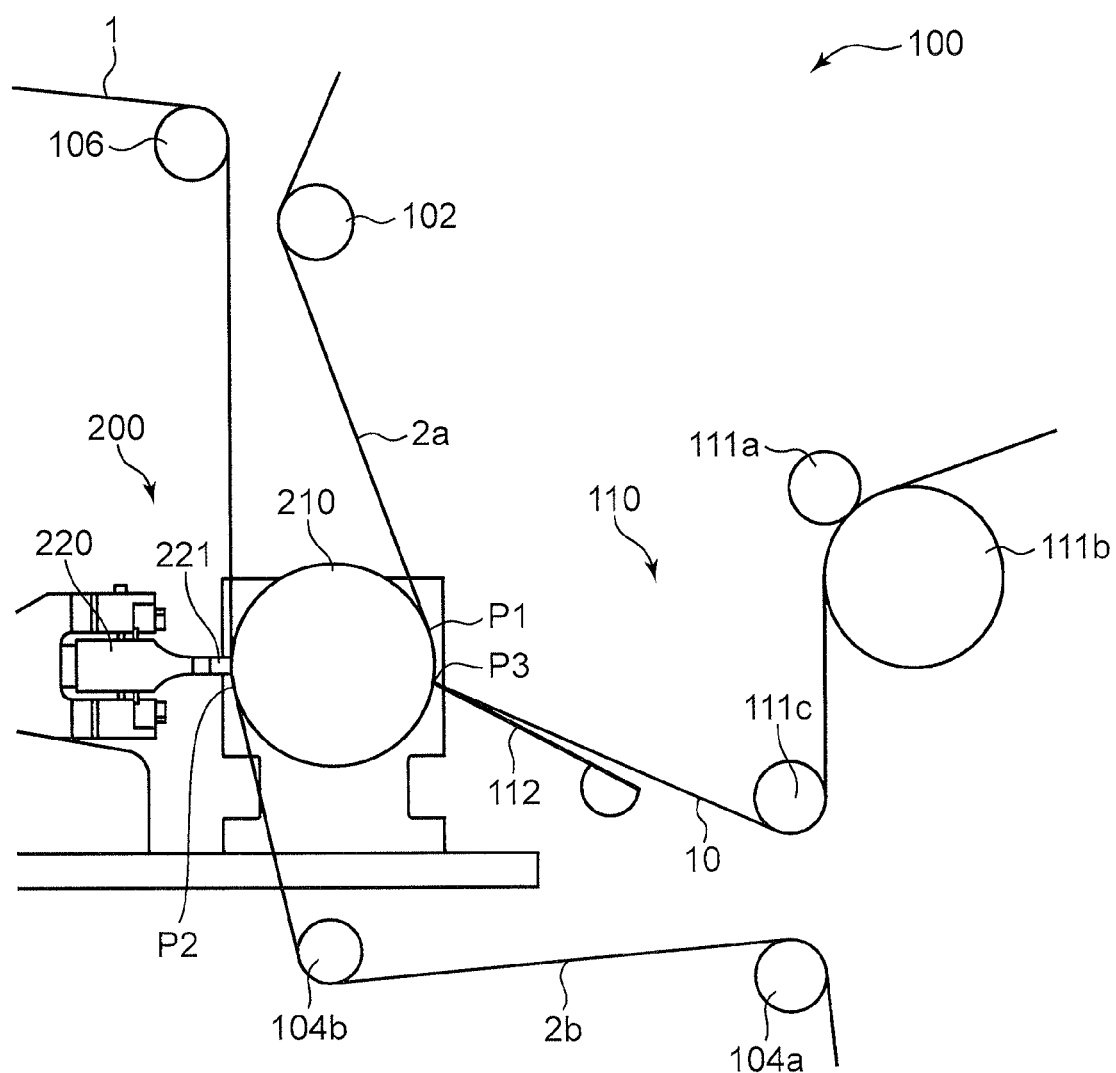
FIG. 6 is a schematic diagram of a production apparatus for the composite stretchable member.

FIG. 6 is a schematic diagram of the production apparatus 100.

The production apparatus 100 comprises: a bonding device 200 for bonding each of the elastic elements 10 to the sheets 2a, 2b and further bonding the sheets 2a, 2b together, by means of ultrasonic welding, in a state in which the elastic elements 10 are sandwiched between the sheets 2a, 2b; a first guide roller (guide device) 102 for guiding the sheet 2a to the bonding unit 200; second guide rollers (guide devices) 104a, 104b for guiding the sheet 2b to the bonding unit 200; an elastic element guide unit (guide device) 110 for supplying the elastic elements 10 to the bonding device 200; and a third guide roller 106 for guiding the bonded sheets and others, i.e., the composite stretchable member 1.

The bonding device 200 comprises an anvil roller (conveyance roller) 210, and a horn (clamping and pressing device) 220.

The anvil roller 210 is a rotary member rotatable about an axis extending in a direction perpendicular to a drawing sheet surface of FIG. 6. This direction orthogonal to the drawing sheet surface of FIG. 6 will hereinafter be referred to as "forward-rearward direction". The anvil roller 210 is operable, when rotated, to convey, on an outer peripheral surface thereof, the sheets 2a, 2b guided by the rollers 102, 104a, 104b and the elastic elements 10 guided by the elastic element guide unit 110 and sandwiched between the sheets 2a, 2b. In the example depicted in FIG. 6, the anvil roller 210 is configured to be rotated in a clockwise direction in FIG. 6. The sheets 2a, 2b sandwiching the elastic elements 10 will hereinafter be referred to occasionally as "pre-bonding sheets". The outer peripheral surface of the anvil roller 210 is formed with a plurality of convex sections 212 (see FIG. 11) each protruding radially outwardly. The derailed structure of the convex sections 212 will be described later.

The horn 220 is a device for giving ultrasonic vibration to the pre-bonding sheets being conveyed by the anvil roller 210, while clamping and pressing the pre-bonding sheets in cooperation with the outer peripheral surface of the anvil roller 210. The horn 220 is disposed to be opposed to the outer peripheral surface of the anvil roller 210. In the example depicted in FIG. 6, it is disposed to be opposed to a left side of the outer peripheral surface of the anvil roller 210. The horn 220 has an output portion 221 provided at a distal end thereof and configured to give ultrasonic vibration toward the outer peripheral surface of the anvil roller 210.

The horn 220 is operable to give ultrasonic vibration to the pre-bonding sheets, while pressing the output portion 221 against the pre-bonding sheets to clamp and press the pre-bonding sheets between the output portion 221 and the anvil roller 210. As a result, the sheets 2a, 2b are melted, and welded together. Further, each of the elastic elements 10 is also melted, so that the melted elastic elements 10 and the melted sheets 2a, 2b are welded together. Specifically, the output portion 221 is capable of clamping and pressing the pre-bonding sheets in cooperation with the aforementioned convex sections 212 to bond the sheets 2a, 2b together and further bond each of the elastic elements to the sheets 2a, 2b, in a region of the pre-bonding sheets disposed on the convex sections 212. The output portion 221 has a planar end face (see FIGS. 13 and 14).

In this embodiment, the covering layers 10b are formed using magnesium stearate having a lower melting point than that of the rubber strings 10a, as mentioned above. Thus, during welding of each of the elastic elements 10 to the sheets 2a, 2b, the covering layers 10b are melted without causing melting of the rubber strings 10a, and welded to the sheets 2a, 2b.

The distal end 221 of the horn 220 extends in the forward-rearward direction so as to enable the horn 220 to give ultrasonic vibration to the outer peripheral surface of the anvil roller 210 in the entire range in a direction of the rotational axis of the anvil roller 210. The horn 220 is operable to constantly give ultrasonic vibration during a period in which the pre-bonding sheets are conveyed by the anvil roller 210. Thus, along with conveyance of the pre-bonding sheets by the anvil roller 210, the pre-bonding sheets are continuously bonded together.

As depicted in FIG. 6, in this embodiment, the sheet 2a is introduced, via the first guide roller 102, onto the outer peripheral surface of the anvil roller 210 at a position P1 on a side opposite to the horn 220. Then, along with rotation of the anvil roller 210, the sheet 2a is conveyed toward the horn 220 along the outer peripheral surface of the anvil roller 210.

On the other hand, by means of the second guide rollers 104a, 104b, the sheet 2b is introduced onto the outer peripheral surface of the anvil roller 210 at a position P2 adjacent to the horn 220 and upstream of the horn 220 in a conveyance direction of the anvil roller 210, and conveyed to a position opposed to the horn 220.

The elastic elements 10 are introduced, via the elastic element guide unit 110, onto the outer peripheral surface of the anvil roller 210 at a position P3 between the position P1 at which the sheet 2a is introduced onto the anvil roller 210 and the position P2 at which the sheet 2b is introduced onto the anvil roller 210. In this way, the elastic elements 10 are conveyed to the position opposed to the horn 220 while being arranged between the sheets 2a, 2b.

The position P2 may be any position between the position P3 and the position opposed to the horn 220. However, it is set preferably to a position on the side of the position opposed to the horn 220, more preferably to a position adjacent to the position opposed to the horn 220. In this case, it becomes possible to prevent occurrence of displacement of the elastic elements 10 introduced onto the outer peripheral surface of the anvil roller 210 caused by the elastic elements 10 being promptly covered by the sheet 2b.

The elastic elements 10 are introduced onto the outer peripheral surface of the anvil roller 210 while lying side-by-side in the forward-rearward direction and in parallel relation to each other, and placed on the sheet 2a being previously conveyed on the outer peripheral surface of the anvil roller 210, while lying side-by-side in the width direction of the sheet 2a and in parallel relation to each other. Further, the elastic elements 10 are introduced onto the anvil roller 210 while being stretched in a circumferential direction of the anvil roller 210. In this embodiment, each of the elastic elements 10 is introduced onto the anvil roller 210 while being stretched by 300% with respect to a natural length thereof (on the assumption that the natural length is 100%).

The elastic element guide unit 110 comprises a plurality of elastic element guide rollers 111a, 111b, 111c, and a guide member 112.

The elastic element guide rollers 111a, 111b, 111c are rotary members each rotatable about an axis extending in the forward-rearward direction, and are configured to guide the elastic elements 10 toward the anvil roller 210 in a state in which each of the elastic elements 10 is stretched by 300% with respect to the natural length.

The guide member 112 is configured to introduce the elastic elements 10 onto the outer peripheral surface of the anvil roller 210, in a state where the plurality of elastic elements 10 are spaced apart from each other in the forward-rearward direction.

Figure 7:
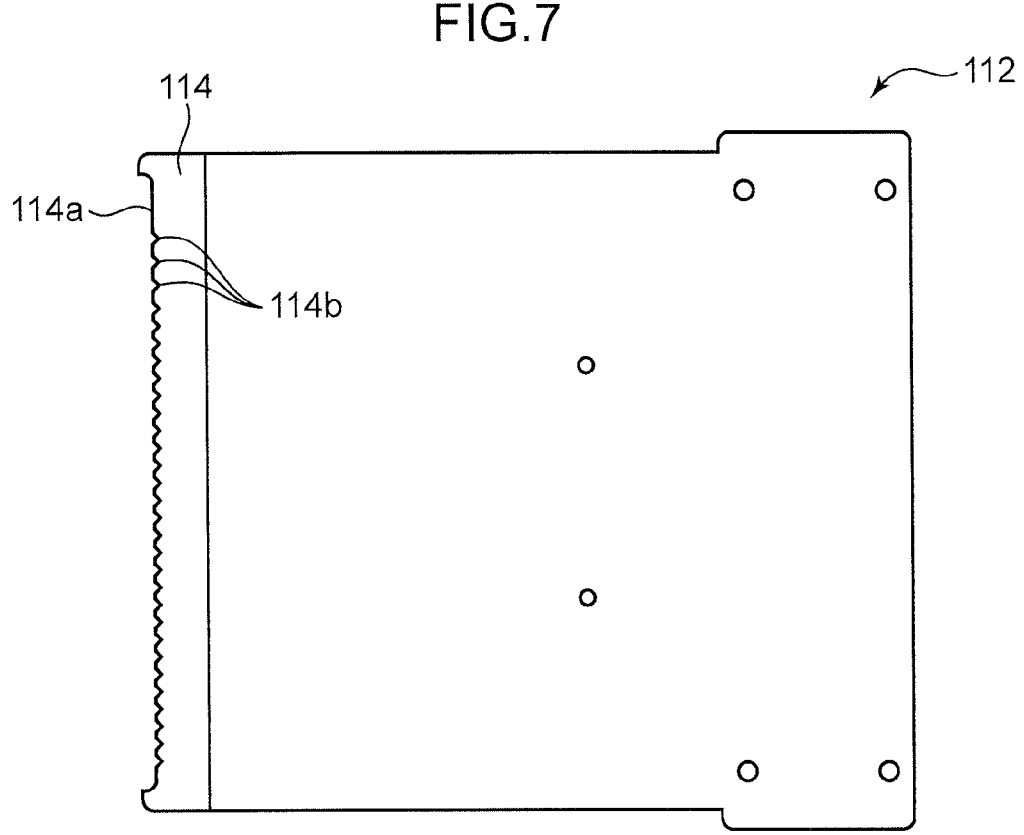
FIG. 7 is a plan view of a guide member.
Figure 8:
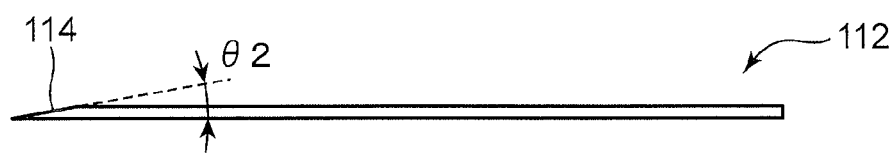
FIG. 8 is a side view of the guide member.

FIG. 7 is a plan view of the guide member 112. FIG. 8 is a side view of the guide member 112.

As depicted in FIGS. 7 and 8 and FIG. 6, the guide member 112 is a flat plate-shaped member. The guide member 112 has a distal edge opposed to the position P3 on the outer peripheral surface of the anvil roller 210, and a base edge disposed farther away from the anvil roller than the distal edge, wherein it is disposed to extend in a direction approaching and separating from the anvil roller 210 and extend in the forward-rearward direction. In this embodiment, in order to prevent interference between the guide member 112 and each of the sheets 2a, 2b, a thickness (in FIG. 8, a dimension in an upward-downward direction) of the guide member 112 is set to a small value, so that the guide member 112 has a thin-plate shape.

A distal edge region (region on the side of the anvil roller 210) of the guide member 112 is formed as an inclined portion 114 inclined to gradually come close to a bottom surface of the guide member 112 in a direction toward the distal edge, i.e., the guide member 112 is formed in a shape tapered toward the distal edge.

Figure 9:
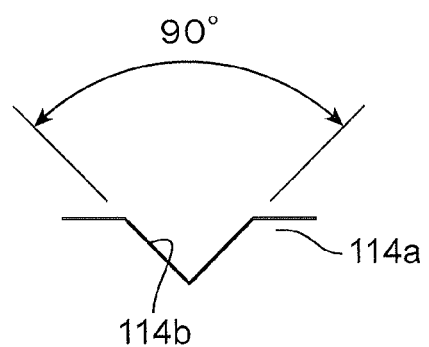
FIG. 9 is an enlarged diagram of a notch of the guide member.

A distal edge 114a of the inclined portion 114, i.e., the distal edge of the guide member 112, has a plurality of notches 114b formed side-by-side in the forward-rearward direction. These notches 114b lie side-by-side at equal intervals in the forward-rearward direction. As depicted in FIG. 9 which enlargedly depicts part of the notches 114b in FIG. 7, each of the notches 114b has a V shape which is concaved from the distal edge 114a of the inclined portion 114 toward the base edge to have an opening angle of 90 degrees. These notches 114b are configured to reliably position and hold the elastic elements 10 so as to guide the elastic elements 10 onto the outer peripheral surface of the anvil roller 210, in a state where the plurality of elastic elements 10 are spaced apart from each other in the forward-rearward direction. Further, the notches 114b are provided in opposed relation to and at the same intervals as those of aftermentioned grooves 214 formed in the anvil roller 210, so as to introduce the elastic elements 10, respectively, into the aftermentioned grooves 214.

Figure 10:
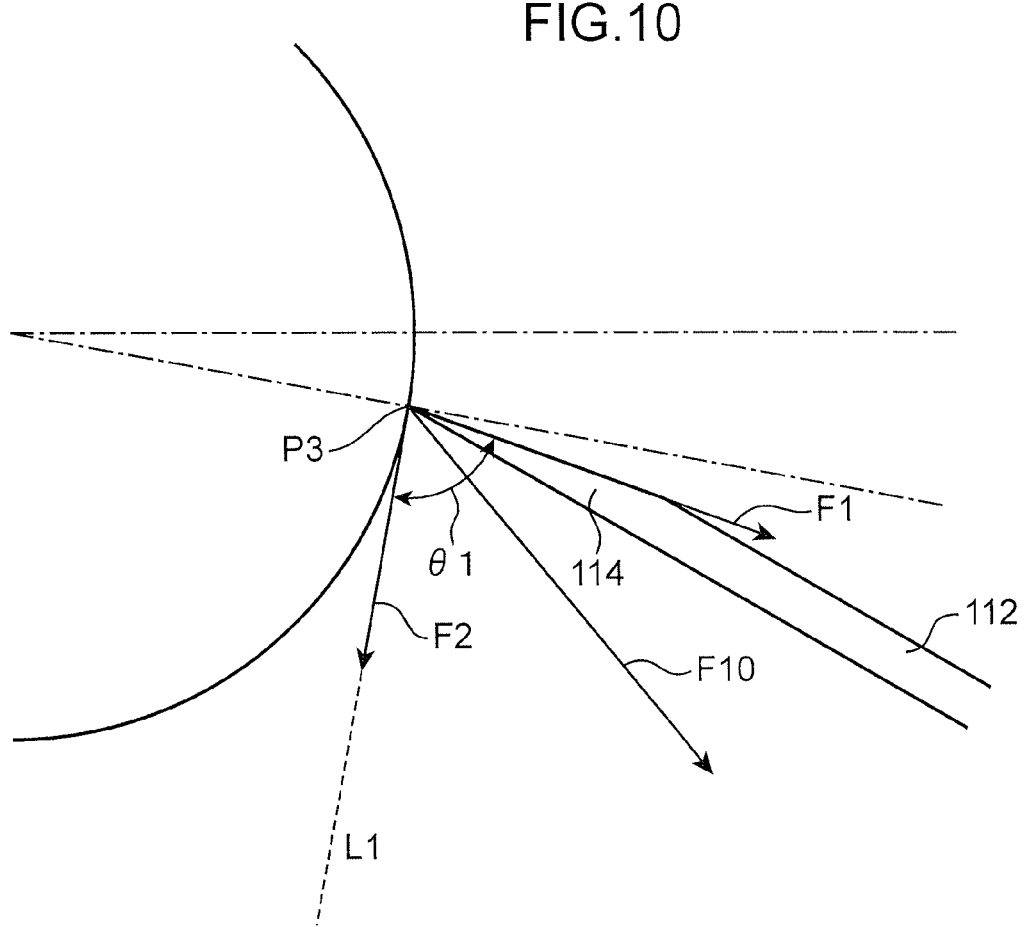
FIG. 10 is an enlarged diagram of part of FIG. 6.

As depicted in FIGS. 6 and 10, the guide member 112 is disposed such that an angle θ1 between a surface of the inclined portion 114 and a line tangent to the anvil roller 210 at the position P3 is 90 degrees or less, in side view. This is intended to suppress disengagement of the elastic elements from the notches 114b.

Specifically, when the angle between the surface of the inclined portion 114 and the line tangent to the anvil roller 210 at the position P3 is set to 90 degrees or less, a resultant force F10 of a force F1 caused by contraction force and applied to each of the elastic elements 10 on the inclined portion 114 (a pulling force acting in a direction separating from the anvil roller 210) and a force F2 applied from the anvil roller 210 to the elastic element 10 at the position P3 (a force F2 along the line tangent to the anvil roller at the position P3) can be set such that it is oriented in a direction approximately opposite to a conveyance direction of the elastic elements 10 on the inclined portion 114 (oriented in a direction toward the base edge of the guide member 112), as depicted in FIG. 10. That is, the resultant force F10 is applied to each of the elastic elements 10, in a direction causing the elastic element 10 to be pressed into a corresponding one of the notches 114b, so that it becomes possible to suppress disengagement of the elastic elements 10 from the notches 114b in the inclined portion 114.

In this embodiment, an angle θ1 between the surface of the inclined portion 114 and a line L1 which is part of the tangent line to the anvil roller 210 passing through the position P3, and located downstream of the position P3 in the conveyance direction of the anvil roller 210, is set to become approximately 90 degrees, and the guide member 112 is set at a position free from interference with the sheets 2a, 2b, as mentioned above. Specifically, in this embodiment, the position P3 is set at a position rotated downstream in the conveyance direction by about 10 degrees with respect to a line passing through a center of the anvil roller 210 and extending horizontally, and an angle θ2 (see FIG. 8) of the inclined portion 114 with respect to the bottom surface of the guide member 112 is set to 10 degrees.

Figure 11:
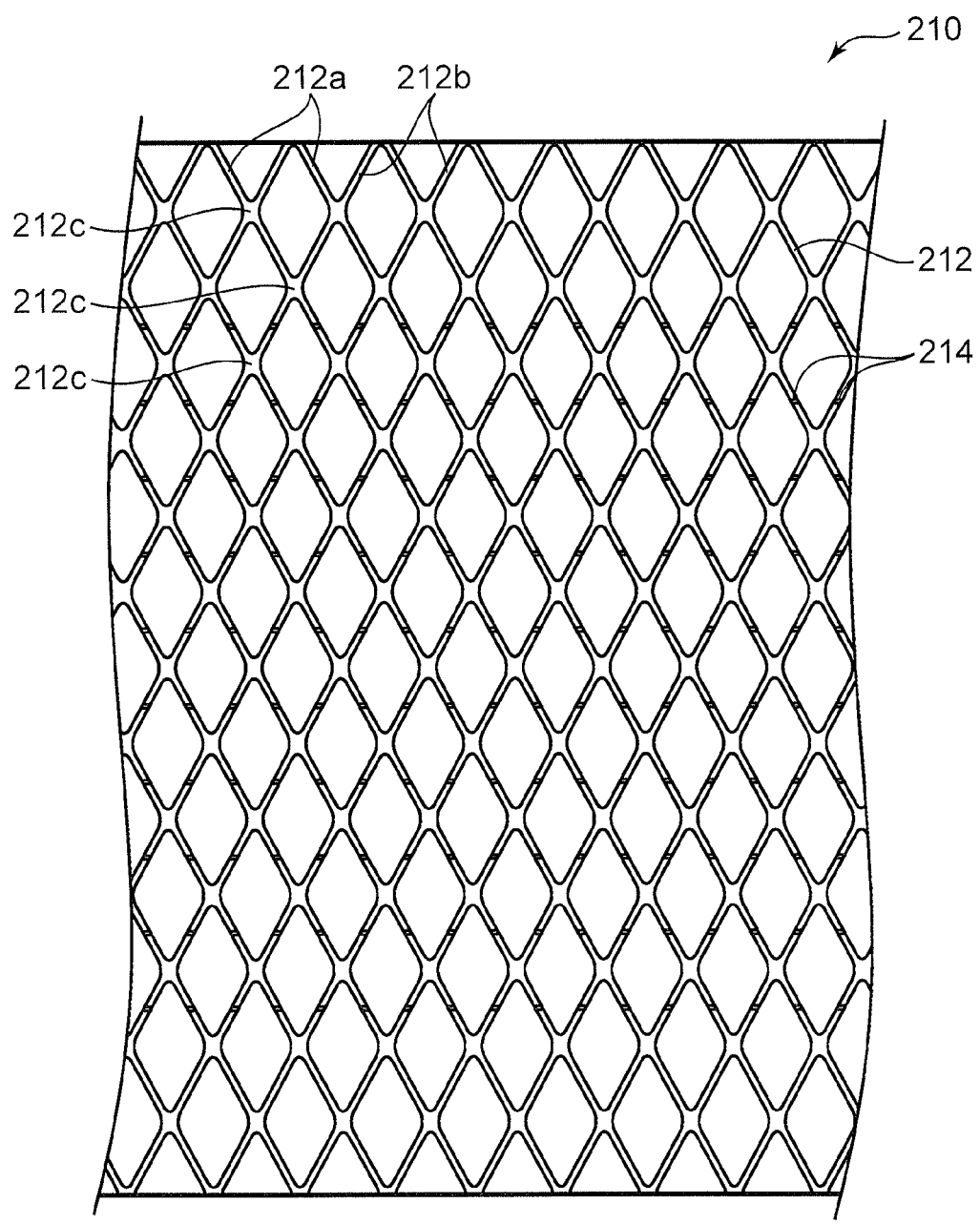
FIG. 11 is a diagram depicting an outer peripheral surface of an anvil roller.

The outer peripheral surface of the anvil roller 210 is formed with the convex sections 212 each protruding radially outwardly, as depicted in FIG. 11. The convex sections 212 are provided on the outer peripheral surface of the anvil roller 210 over the entire circumferential direction thereof. The convex sections 212 have a shape corresponding to that of the bonding sections 4. In this embodiment, the bonding sections 4 have a diamond-lattice pattern as mentioned above, and correspondingly the convex sections 212 have a diamond-lattice pattern.

Specifically, the convex sections 212 comprise a first convex section 212a for forming the first bonding section 4a, and a second convex section 212b for forming the second bonding section 4b.

The first convex section 212a extends along a direction (first direction) intersecting the circumferential direction of the anvil roller 210 (conveyance direction of the anvil roller 210), i.e., along a line intersecting the circumferential direction, and a plurality of the first convex sections 212a are arranged in parallel relation to each other and at equal intervals in the circumferential direction. The second convex section 212b extends along a direction (second direction) intersecting the circumferential direction of the anvil roller 210 and the first direction, i.e., along a line intersecting the circumferential direction, and a plurality of the second convex sections 212b are arranged in parallel relation to each other and at equal intervals in the circumferential direction of the anvil roller 210.

Each of the first convex sections 212a and the second convex sections 212b is inclined at an angle of less than 45 degrees with respect to the forward-rearward direction, and the intersecting convex sections are inclined in symmetrical relation to each other with respect to the forward-rearward direction. Further, a spaced-apart distance between adjacent ones of the first convex sections 212a is coincident with a spaced-apart distance between adjacent ones of the second convex sections 212b, and intersection points 212c of the first convex sections 212a with the second convex sections 212b lie side-by-side at equal intervals on each of two line extending, respectively, in the forward-rearward direction and the circumferential direction of the anvil roller 210.

Figure 12:
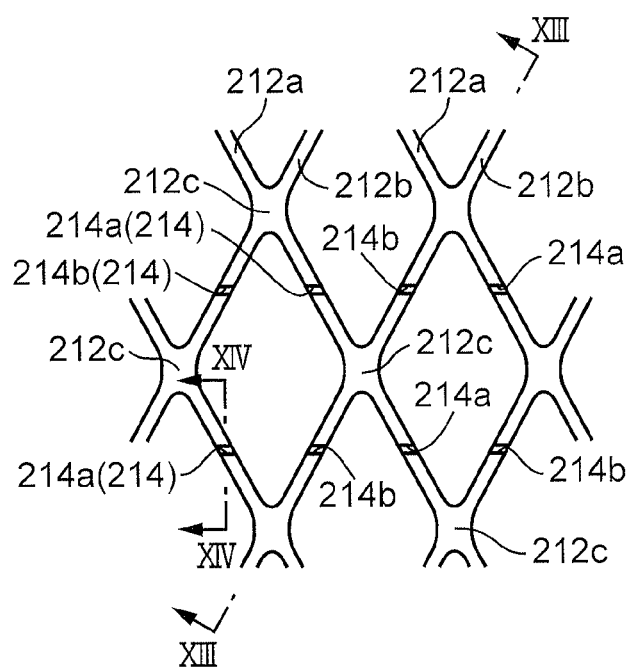
FIG. 12 is a diagram enlargedly depicting part of FIG. 11.
Figure 13:
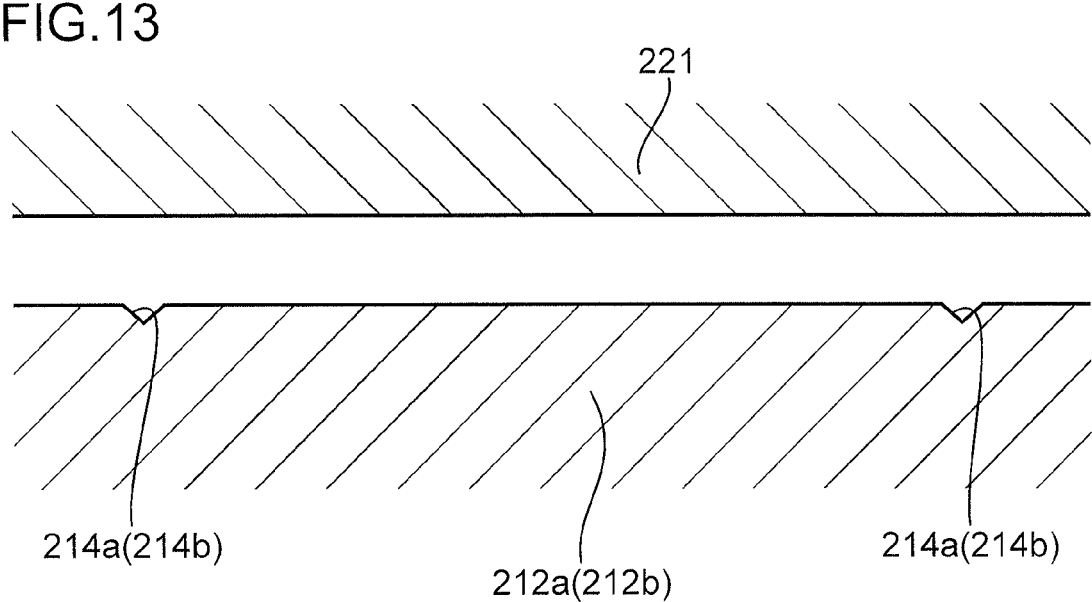
FIG. 13 is a sectional view taken along the line XIII-XIII in FIG. 12.
Figure 14:
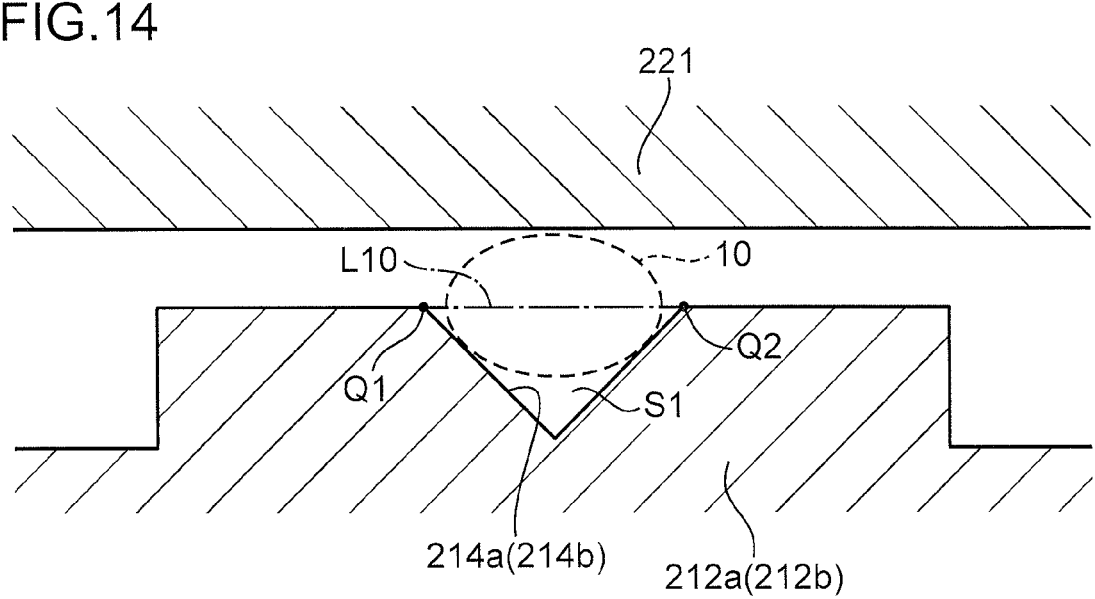
FIG. 14 is a sectional view taken along the line XIV-XIV in FIG. 12.

As depicted in FIG. 12 which is an enlarged view of part of FIG. 11, FIG. 13 which is a sectional view taken along the line XIII-XIII in FIG. 12, and FIG. 14 which is a sectional view taken along the line XIV-XIV in FIG. 12, each of the first convex sections 212a and the second convex sections 212b is formed with a plurality of grooves 214 (214a, 214b) each concaved inwardly in a radial direction of the anvil roller 210. As depicted, for example, in FIG. 13, each of the first convex sections 212a and the second convex sections 212b is formed with a plurality of grooves 214 at positions spaced apart from each other in a longitudinal direction thereof.

A plurality of regions of the sheet 2a (sheet disposed on the side of the anvil roller 210) on each of which a respective one of the elastic elements 10 will lie are inserted, respectively, in a plurality of groups of the grooves 214. Therefore, the arrangement of the elastic elements 10 with respect to the bonding sections 4 is identical to the arrangement of the groups of grooves with respect to the convex sections 212.

Specifically, in this embodiment, as depicted in FIG. 12, a groove (first groove) 214a extending in the circumferential direction of the anvil roller 210 is formed in each of the first convex sections 212a, at a position between adjacent ones of the intersection points 212c with the second convex sections 212b, more specifically, at a central position between the adjacent intersection points 212c. Similarly, a groove (second groove) 214b is formed in each of the second convex sections 212b, at a position between adjacent ones of the intersection points 212c with the first convex sections 212a, more specifically, at a central position between the adjacent intersection points 212c. Further, a plurality of the grooves 214 are provided on a line extending along the circumferential direction of the anvil roller 210 at equal intervals, and provided on a line extending along the forward-rearward direction at equal intervals.

The sheet 2a is conveyed by the anvil roller 210, in a state in which the regions of the sheet 2a on each of which a respective one of the elastic elements 10 lies are inserted, respectively, in grooves 214. As mentioned above, in this embodiment, each of the elastic elements 10 is introduced into a respective one of the grooves 214 by the guide member 112 having the notches 114 provided at respective positions corresponding to the grooves 214, so that the elastic elements 10 are stably disposed, respectively, at appropriate positions on the sheet 2a.

In this embodiment, the sheet 2a is conveyed by the anvil roller 210, in a state in which each of the elastic elements 10 is partially inserted in a respective one of the grooves 214, together with part of the sheet 2a. It should be noted that the sheet 2a may be conveyed in a state in which only the part of the sheet 2a is inserted.

As above, the grooves 214 are formed, respectively, in the regions of the convex sections 212 on each of which a respective one of the elastic elements 10 will lie. Thus, when the pre-bonding sheets are clamped and pressed during bonding, at least part of each of the elastic elements 10 arranged between the pre-bonding sheets is moved into a corresponding one of the grooves in an escaping manner. This makes it possible to avoid breakage of the elastic elements 10 during clamping and pressing.

However, if each of the grooves 214 has an excessively large cross-sectional area, it could become difficult to appropriately bond each of the elastic elements 10 to the sheets 2a, 2b. For this reason, in this embodiment, as depicted in FIG. 14, each of the elastic elements 10 having a natural length is disposed in a corresponding one of the grooves 214, in such a manner that part of the elastic element 10 protrudes outside the grooves 214, and the remaining part of the elastic element 10 is received in the grooves 214. More specifically, a cross-sectional shape of the groove 214 cut along a plane orthogonal to the circumferential direction (conveyance direction) of the anvil roller 210 is set such that, in the state in which the elastic element 10 having a natural length is disposed in the groove 214, part of the elastic element 10 protrudes outwardly in the radial direction of the anvil roller 210, with respect to a linear imaginary line (one-dot chain line) L10 connecting opening edges (Q1, Q2) of the groove 214. Further, the above cross-sectional shape of the groove 214 is set such that, when the elastic element 10 being stretched by 300% is disposed in the groove 214, part of the elastic element 10 protrudes outwardly in the radial direction of the anvil roller 210, with respect to the linear imaginary line L10 connecting the opening edges (Q1, Q2) of the groove 214. Such a cross-sectional shape of the groove 214 is preferably an approximately V shape, as depicted in FIG. 14. Further, a cross-sectional area S1 of the groove 214 is preferably set to be less than a cross-sectional area of the elastic element 10 to be disposed therein.

(3) Production Method

A method of producing the composite stretchable member 1 using the production apparatus 100 configured as described above comprises a guide step and a bonding step.

The guide step includes: guiding the sheet 2a to the bonding device 200 by the first guide roller 102; guiding the sheet 2b to the bonding device 200 by the second guide rollers 104a, 104b; and guiding the elastic elements 10 to the bonding device 200 by the elastic element guide unit 110. Further, in the guide step, the sheets 2a, 2b and the elastic elements 10 are conveyed to the bonding device 200, in a state in which the elastic elements 10 are sandwiched between the sheets 2a, 2b while being arranged to extend in the longitudinal direction of the sheets 2a, 2b in parallel relation to each other.

In this embodiment, the sheets 2a, 2b and the elastic elements 10 are guided to the outer peripheral surface of the anvil roller 210, as mentioned above.

Further, by the guide member 112, the regions of the sheet 2a on each of which a respective one of the elastic elements 10 lies, and parts of the elastic elements 10, are introduced, respectively, into the grooves 214 formed in the convex sections 212.

The bonding step includes: clampingly pressing the pre-bonding sheets, i.e., the sheets 2a, 2b between which the elastic elements 10 are sandwiched, by the horn 220 and the convex sections 212; and, in this state, giving ultrasonic vibration from the horn 220 toward the convex sections 212 to bond each of the elastic elements 10 to the sheets 2a, 2b and further bond the sheets 2a, 2b together, by means of ultrasonic welding. In this process, associated ones of the regions of the anvil roller-side sheet 2a on each of which a respective one of the elastic elements 10 lies, and parts of the elastic elements 10, are partially welded together, in the state in which they are inserted in a corresponding one of the grooves 214.

(4) Wearable Article and Production Method Therefor

Figure 15:
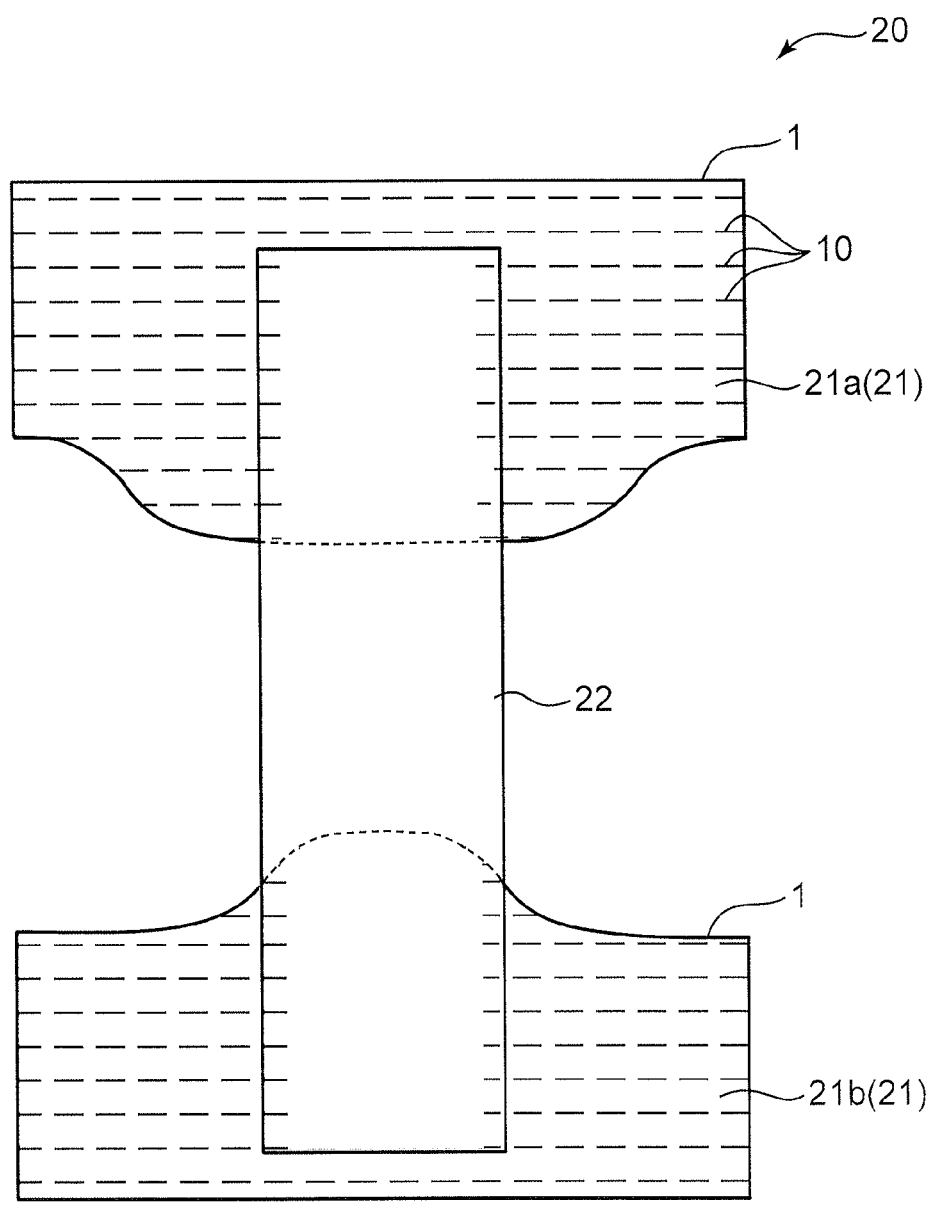
FIG. 15 is a developed diagram of a disposable diaper using the composite stretchable member.

FIG. 15 is a schematic diagram depicting a disposable diaper (wearable article) 20 using the composite stretchable member 1 configured as described above, as a usage example of the composite stretchable member 1.

The disposable diaper 20 comprises: a waist portion 21 having a front abdominal portion 21a to be disposed on a front side of an abdominal region of a wearer, and a rear dorsal portion 21b to be disposed on the side of a hip region of the wearer; and a crotch portion 22 to be disposed along a crotch region of the wearer. The composite stretchable member 1 according to this embodiment is used in the front abdominal portion 21a and the rear dorsal portion 21b. For example, the composite stretchable member 1 is applied to the front abdominal portion 21a and the rear dorsal portion 21b in such a manner that a stretchable direction of the composite stretchable member 1 is coincident with a waist circumferential direction during wearing (a rightward-leftward direction in FIG. 15).

Figure 16:
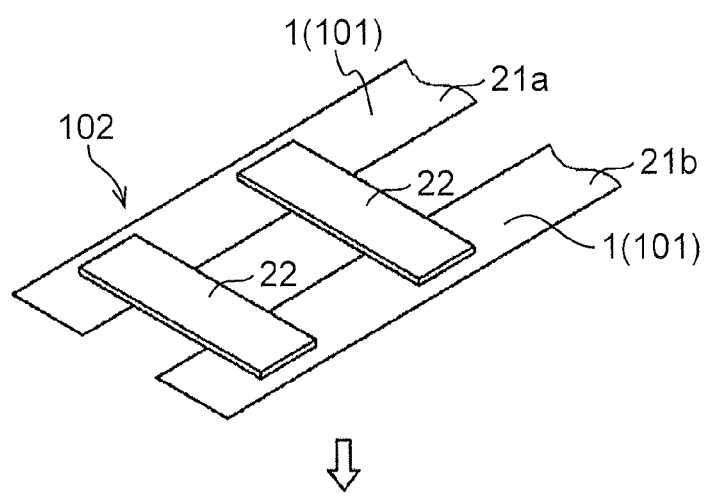
FIG. 16 is a diagram for explaining a production method for the disposable diaper depicted in FIG. 15.
Figure 16:
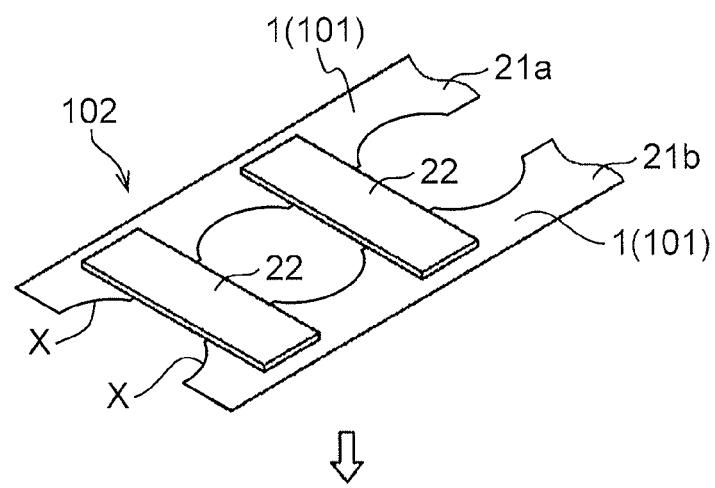
Figure 16:
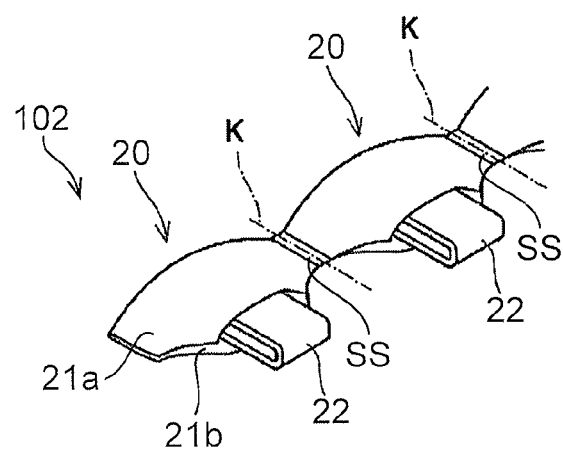

FIG. 16 is a diagram illustrating a production method for the disposable diaper 20. This production method comprises stages 1 to 3. In the stage 1, one pair of continuous bodies 101 of the composite stretchable member 1 extending in a conveyance direction are prepared. That is, a continuous body 101 for forming the front abdominal portion 21a and a continuous body 101 for forming the rear dorsal portion 21b are prepared. Then, the pair of continuous bodies 101 are conveyed in a longitudinal direction of each of the continuous bodies 101 while being arranged parallel to each other, and the crotch portion 22 is placed to straddle the pair of continuous bodies 101, in such a manner that a longitudinal direction of the crotch portion 22 is oriented orthogonal to the longitudinal direction of the continuous body 101. For example, a plurality of the crotch portions 22 are placed in spaced-apart relation in the conveyance direction. Then, the crotch portions 22 and the continuous bodies 101 are bonded together to form a bonded body 102 (bonded body forming step).

Subsequently, in the stage 2, a hole serving as a leg opening is formed between adjacent ones of the crotch portions 22. Then, the bonded body 102 is double-folded along a folding line defined by a center line of the bonded body 102 in a width direction (a direction orthogonal to the longitudinal direction of the continuous body 101), in such a manner that each of the crotch portions 22 is located inward of the continuous bodies 101 (double-folding step).

Subsequently, in the stage 3, superimposed portions of the continuous bodies 101 at an intermediate position between adjacent ones of the crotch portions 22 are bonded together along a direction orthogonal to the longitudinal direction of the continuous body 101, to thereby form a side seal (side sealing step), and the continuous bodies 101 are cut along a cutting line K in the side seal (cutting step).

In this way, the disposable diaper 20 is produced in which the waist portion 21 (the front abdominal portion 21a and the rear dorsal portion 21b) is formed of the composite stretchable members 1 so as to be stretchable in the waist circumferential direction.

In this embodiment, the sub-step of providing a hole serving as a leg opening may be performed before bonding the crotch portions 22 to the continuous bodies 101, or needs not necessarily be performed. Further, each of the elastic elements 10 of the composite stretchable member 1 may be bonded to the two sheets 2a, 2b by a hot-melt adhesive, in a vicinity of a region corresponding to the cutting line K. This makes it possible to prevent drop-off of the elastic elements 10 due to cutting along the cutting line K.

As described above, the composite stretchable member 1 according to this embodiment comprises two sheets 2a, 2b which are bonded together in a plurality of bonding sections 4 each configured to extend along a line intersecting a stretchable direction of the composite stretchable member 1 and a plurality of elastic elements 10, wherein each of the plurality of elastic elements 10 is sandwiched between the sheets 2a, 2b to extend along the stretchable direction of the composite stretchable member 1 and intersect the bonding sections 4, and bonded to the sheets 2a, 2b at intersection points 4d, 4e.

That is, the sheets 2a, 2b are continuously bonded together in a plurality of bonding sections 4, along a line intersecting the stretchable direction of the composite stretchable member 1, i.e., a longitudinal direction of the sheets 2a, 2b, and each of the elastic elements 10 is bonded to the sheets 2a, 2a, in the plurality of bonding sections 4.

Thus, it becomes possible to increase respective bonding forces between the sheets 2a, 2b and between associated ones of the elastic elements 10 and the sheets 2a, 2b to thereby prevent debonding between the sheets 2a, 2h or between associated ones of the sheets 2a, 2b and the elastic elements 10, during use or the like. In particular, it is possible to highly ensure a bonding force in a direction intersecting the stretchable direction of the composite stretchable member 1. Thus, in the case where the composite stretchable member 1 is used to a portion (waist portion 21) of a wearable article such as a disposable diaper, for covering a waist region of a wearer, in such a manner that the stretchable direction of the composite stretchable member 1 is coincident with the waist circumferential direction, as mentioned above, it becomes possible to suppress a situation where the sheets 2a, 2b or associated ones of the sheets 2a, 2b and the elastic elements 10 are debonded from each other when the waist portion is pulled up and down during attaching and removing of the wearable article.

Although the above embodiment has been described based on an example where all of the plurality of elastic elements 10 intersect the bonding sections 4, the composite stretchable member may be configured such that only part of the elastic elements 10 intersect the bonding sections 4.

The composite stretchable member 1 is used in the waist portion 21 of the disposable diaper 22. Thus, it is possible to ensure stretchability of the waist portion 21 to provide good wearing comfort, while suppressing breakage of the waist portion 21 during attaching and removing of the disposable diaper 22.

Although the above embodiment has been described based on an example where the waist portion 21 is entirely composed of the composite stretchable member 1, the composite stretchable member 1 may be used in only part of the waist portion 21.

Further, the above embodiment can bring out the following advantageous effects.

In the above embodiment, the bonding sections 4 comprise a plurality of first bonding sections 4a extending parallel to each other along a direction intersecting the longitudinal direction of the sheets 2a, 2b (the stretchable direction of the composite stretchable member 1), and a plurality of second bonding sections 4b extending parallel to each other along a direction intersecting the longitudinal direction of the sheets 2a, 2b and each intersecting the first bonding sections 4a.

That is, the sheets 2a, 2b are bonded together in the two types of bonding sections 4a, 4b extending in different directions. Thus, even in a situation where an external force is applied to the composite stretchable member 1 from various directions, it is possible to more reliably suppress debonding between the sheets 2a, 2b or between associated ones of the sheets 2a, 2b and the elastic elements 10. In the above embodiment, the first bonding sections 4a and the second bonding sections 4b intersect each other, so that it is possible to increase a bonding force of the composite stretchable member 1 at each of the intersection points 4c, and thus a bonding force between the sheets 2a, 2b at a position adjacent to each of the intersection points 4c.

In the above embodiment, each of a longitudinal direction (first direction) of each of the first bonding sections 4a and a longitudinal direction (second direction) of each of the second bonding sections 4b is set to intersect a direction orthogonal to the longitudinal direction of the sheets 2a, 2b (the stretchable direction of the composite stretchable member 1).

Thus, when an external force is applied in the longitudinal direction of the sheets 2a, 2b, it is possible to reduce a normal component of the external force with respect to each of the bonding sections 4a, 4b and thus reduce a force to be applied in a direction perpendicular to each of the bonding sections 4a, 4b. This makes it possible to more reliably suppress debonding between the sheets 2a, 2b in the bonding sections 4a, 4b.

In the above embodiment, each of the first bonding sections 4a and the second bonding sections 4b is inclined at an angle of less than 45 degrees, with respect to the width direction of the sheets 2a, 2b (a direction orthogonal to the stretchable direction of the composite stretchable member 1).

Thus, it is possible to reduce a distance between the intersection points 4d, 4e of each of the elastic elements 10 with the bonding sections 4a, 4b, i.e., a distance between the bonded points 4d, 4e of each of the elastic elements 10 to the sheets 2a, 2b (a distance between adjacent ones of the bonded points 4d, 4e) in the longitudinal direction of the sheets 2a, 2b (the stretchable direction of the composite stretchable member 1). This makes it possible to more finely form gathers between the bonded points 4d, 4e in the longitudinal direction of the sheets 2a, 2b (the stretchable direction of the composite stretchable member 1), in a non-stretched state of the composite stretchable member 1. Therefore, it is possible to provide a better feel.

In the above embodiment, the intersection points 4c of the first bonding sections 4a with the second bonding sections 4b lie in a straight line extending in the longitudinal direction of the sheets 2a, 2b (the stretchable direction of the composite stretchable member 1), and lie side-by-side on a straight line extending in the width direction of the sheets 2a, 2b (the direction orthogonal to the stretchable direction of the composite stretchable member 1).

Thus, the intersection points 4c between the first and second bonding sections 4a, 4b can be arranged in an orderly manner, so that it is possible to form gathers between adjacent ones of the intersection points 4c in a regular pattern so as to provide good appearance, and to increase a bonding force between the sheets 2a, 2b in the longitudinal direction of the sheets 2a, 2b (the stretchable direction of the composite stretchable member 1) and in the width direction of the sheets 2a, 2b.

Although each of the elastic elements 10 may be disposed to intersect the first bonding sections 4a and the second boding sections 4b at the intersection points 4c of the first bonding sections 4a with the second bonding sections 4b, in the above embodiment each of the elastic elements 10 is disposed such that it intersects the first bonding sections 4a and the second boding sections 4b at points other than the intersection points 4c.

That is, each of the elastic elements 10 is bonded to the sheets in the first bonding sections 4a and the second boding sections 4b, individually. In this case, as compared to the case where each of the elastic elements 10 is disposed to intersect the bonding sections 4a, 4b at the intersection points 4c therebetween, it is possible to increase the number of bonded points of each of the elastic elements 10 to the sheets 2a, 2b. This makes it possible to increase a bonding force between associated ones of the elastic elements 10 and the sheets 2a, 2b.

In the above embodiment, first elastic element-side intersection points 4d which are intersection points of the elastic elements 10 with the first bonding sections 4a, and second elastic element-side intersection points 4e which are intersection points of the elastic elements 10 with the second bonding sections 4b, lie in a straight line extending in the width direction of the sheets 2a, 2b (the direction orthogonal to the stretchable direction of the composite stretchable member 1).

Thus, it is possible to form gathers between adjacent ones of the bonded points of each of the elastic elements 10 to the sheets 2a, 2b, i.e., between adjacent ones of the elastic element-side intersection points 4d, 4e, in such a manner as to lie in a straight line extending in the width direction of the sheets 2a, 2b, thereby providing good appearance. Further, it is possible to provide a better feel in this direction.

In the above embodiment, intersection points of each of the elastic elements 10 with the bonding sections 4, i.e., bonded points of each of the elastic elements 10 to the sheets 2*a*, 2*b* are arranged at equal intervals in the longitudinal direction of the sheets 2*a*, 2*b* (the stretchable direction of the composite stretchable member 1). That is, each of the elastic elements 10 intersects the bonding sections 4 at equal intervals in the longitudinal direction of the sheets 2*a*, 2*b*.

Thus, sizes of gathers formed between adjacent ones of the bonded points 4*d*, 4*e* of each of the elastic elements 10 to the sheets 2*a*, 2*b*, specifically, dimensions of the gathers protruding outwardly, i.e., in a direction perpendicular to the sheets 2*a*, 2*b*, can be uniformed in the longitudinal direction of the sheets 2*a*, 2*b* (the stretchable direction of the composite stretchable member 1). This makes it possible to provide good appearance and good feel.

In the above embodiment, each of the elastic elements 10 comprises a plurality of elastic bodies 10*a*, and a plurality of covering layers 10*b* each covering a respective one of the elastic bodies 10*a*, wherein each of the elastic elements 10 is bonded to the sheets 2*a*, 2*b* in such a manner that the covering layers 10*b* are welded to the sheets 2*a*, 2*b*.

This makes it possible to suppress breakage of the elastic elements 10 due to clamping and pressing during bonding.

It should be noted that the present invention is not limited to the above embodiment. For example, the following embodiments may be employed.

One of the group of first bonding sections 4*a* and the group of second bonding sections 4*b* may be omitted. In this case, the bonding sections 4 may be formed to extend in a direction orthogonal to the longitudinal direction of the sheets 2*a*, 2*b*.

Figure 17:
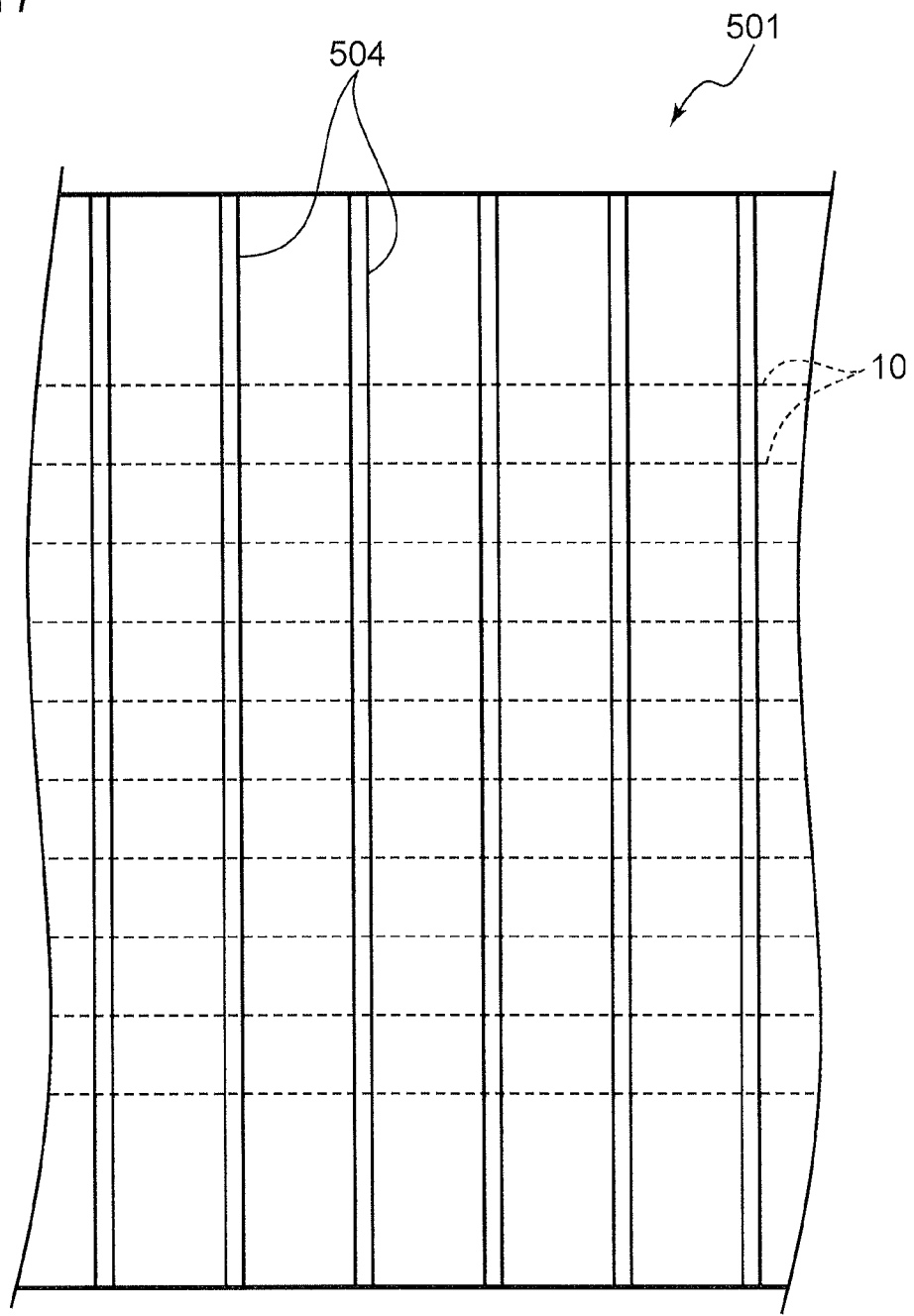
FIG. 17 is a plan view of a composite stretchable member according to another embodiment of the present invention.

That is, as depicted in FIG. 17, a plurality of bonding sections 504 may be formed to extend along the width direction of the sheets 2*a*, 2*b* (a direction orthogonal to a stretchable direction of a composite stretchable member 501).

This makes it possible to increase a bonding force between the sheets 2*a*, 2*b*, in the width direction of the sheets 2*a*, 2*b* (the direction orthogonal to the stretchable direction of the composite stretchable member 501).

More specifically, for enabling the bonding sections 504 to have a pattern depicted in FIG. 17, it is necessary to arrange a plurality of convex sections in the conveyance direction of the anvil roller 210 in parallel relation to each other. In this case, the output portion 221 of the horn 211 will intermittently come into contact with the convex sections. This is likely to cause large vibration and noise.

Figure 18:
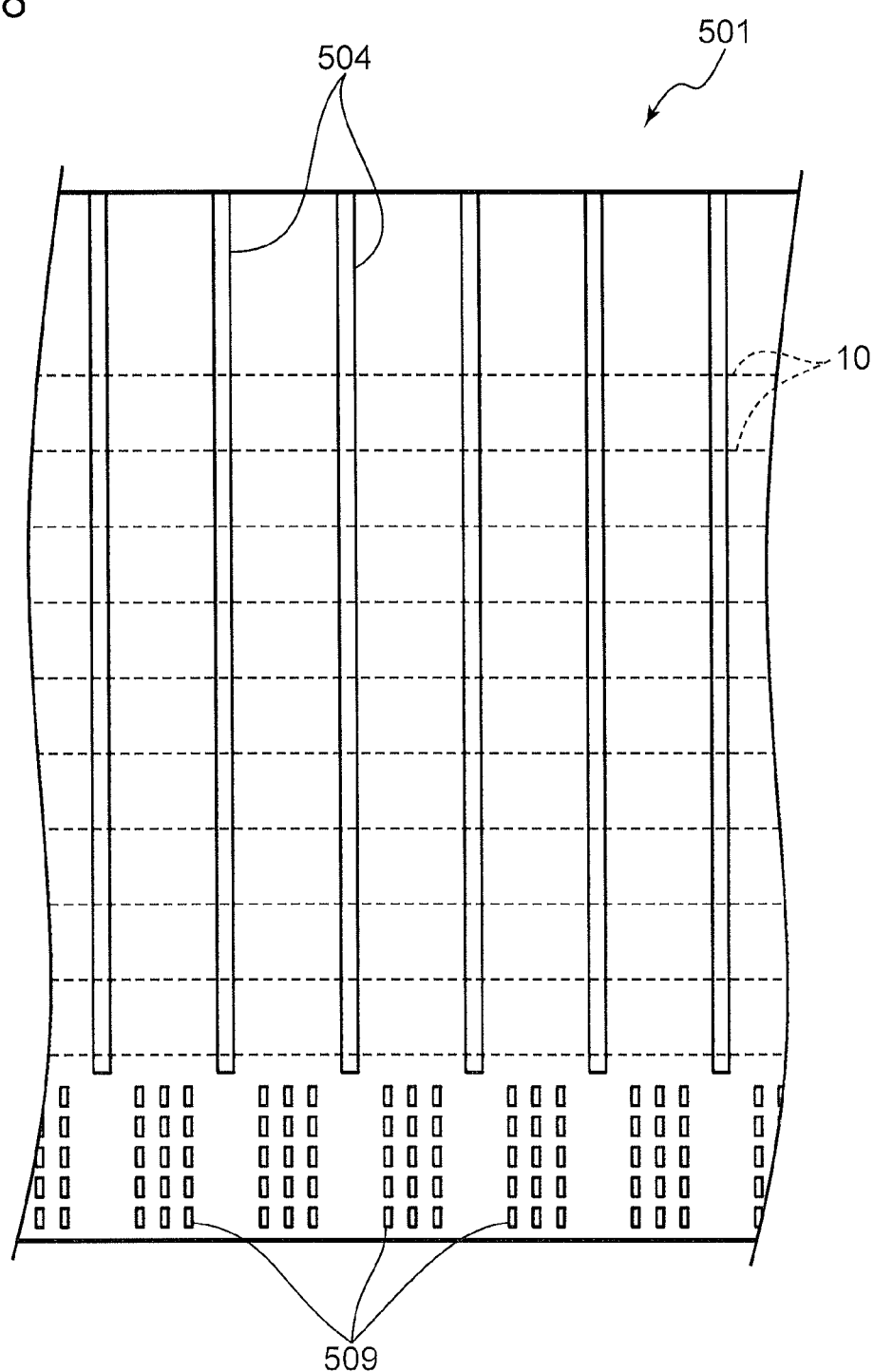
FIG. 18 is a plan view of a composite stretchable member according to yet another embodiment of the present invention.

For this reason, in the case where each of the bonding sections 504 is provided to extend along the width direction of the sheets 2*a*, 2*b*, it is preferable to provide an auxiliary seal 509 in an edge region located in the width direction of the sheets 2*a*, 2*b*, as depicted in FIG. 18.

Specifically, in addition to the convex sections 504 (for details, a plurality of convex sections corresponding to the bonding sections 504) for bonding the sheets 2*a*, 2*b* together while sandwiching the elastic elements 10 therebetween, an auxiliary convex section 509 (for details, a convex section corresponding to the auxiliary seal 509) for bonding only the sheets 2*a*, 2*b* together is provided in an edge region of the outer peripheral surface of the anvil roller 210 in a width direction of the anvil roller 210 (in a direction parallel to the rotational axis of the anvil roller 210). Further, the auxiliary convex section 509 is provided between adjacent ones of the convex sections 504 in the conveyance direction of the anvil roller 210.

In the example depicted in FIG. 18, a plurality of (in the example depicted in FIG. 18, five) auxiliary convex sections 509 are provided in spaced-apart relation to each other in the width direction of the anvil roller 210 to form a line, and three lines of the plurality of auxiliary convex sections 509 are provided between adjacent ones of the convex sections 504 in the conveyance direction of the anvil roller 210.

Thus, it becomes possible to enable the output portion 221 of the horn 220 to continuously come into contact with a plurality of convex sections comprising the convex sections 504 and the auxiliary convex sections 509. This makes it possible to keep down noise and vibration which would otherwise occur when the output portion 221 of the horn 220 starts to come into contact with each of the convex sections.

The auxiliary convex section 509 may be formed continuously along the conveyance direction of the anvil roller 210. In this case, it is possible to more reliably enable the output portion 221 of the horn 220 to continuously come into contact with the convex sections. However, the auxiliary convex section 509 has a relatively small dimension in the width direction of the anvil roller 210. Thus, during contact between the auxiliary convex section 509 and the output portion 221 of the horn 220, a relatively large force is applied to a region of the sheets 2*a*, 2*b* clamped therebetween, so that the sheets 2*a*, 2*b* are likely to undergo breakage. As one example, in the case where the auxiliary convex section 509 is continuously provided along the conveyance direction of the anvil roller 210, as mentioned above, the sheets 2*a*, 2*b* are likely to be broken along the auxiliary convex section 509, and divided into a portion in contact with the auxiliary convex section 509 and the remaining portion. Therefore, when there is a risk of breakage of the sheets 2*a*, 2*b*, it is preferable to intermittently provide a plurality of auxiliary convex sections 509, as depicted in FIG. 18.

Further, after passing through the anvil roller 210, the region of the sheets 2*a*, 2*b* formed with the auxiliary convex sections 509 may be cut off, or may be used as part of the composite stretchable member 501.

Figure 19:
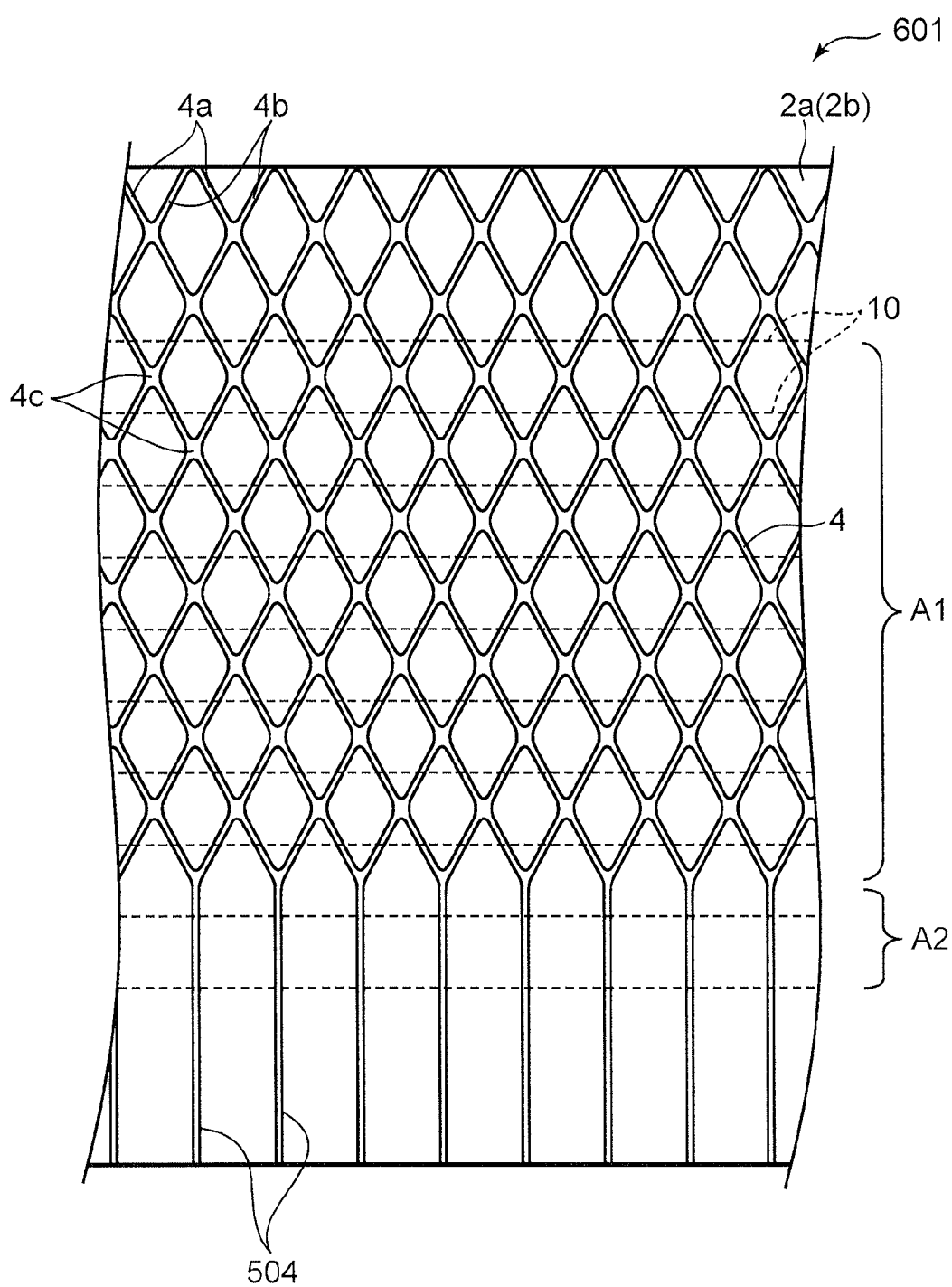
FIG. 19 is a plan view of a composite stretchable member according to still another embodiment of the present invention.

Further, as depicted in FIG. 19, each of the sheets 2*a*, 2*b* (stretchable member 601) may be formed to have an intersecting pattern region A1 with a plurality of bonding sections comprising the first bonding sections 4*a* and the second bonding sections 4*b*, and a straight pattern region A2 comprising a plurality of bonding sections (third bonding sections) 504 each extending along the width direction of the sheets 2*a*, 2*b*, as depicted in FIG. 17, wherein each of the bonding sections 504 extends from a respective one of part of intersection points of the first bonding sections 4*a* with the second bonding sections 4*b*, in the width direction. This makes it possible to increase a bonding force between the sheets 2*a*, 2*b* along the width direction in the straight pattern region A2, while increasing a bonding force between the sheets 2*a*, 2*b* along a direction intersecting the width direction in the intersecting pattern region A1.

These sheets 2*a*, 2*b* may be applied to a waist portion of a wearable article such as the aforementioned disposable diaper 20, wherein the straight pattern region A2 may be disposed in an edge region of the waist portion in such a manner that each of the bonding sections 504 extends to an edge of the waist portion from a inwardly portion. In this case, gathers formed in the intersecting pattern region A1 can provide good appearance and good feel, and gathers formed in the straight pattern region A2 can form open spaces opened outwardly from the edge of the waist portion to provide good breathability. That is, in the straight pattern region A2, passages providing fluid communication between an inside and an outside of the waist portion are formed between adjacent ones of the bonding sections 504, so that it is possible to provide good breathability.

Figure 20:
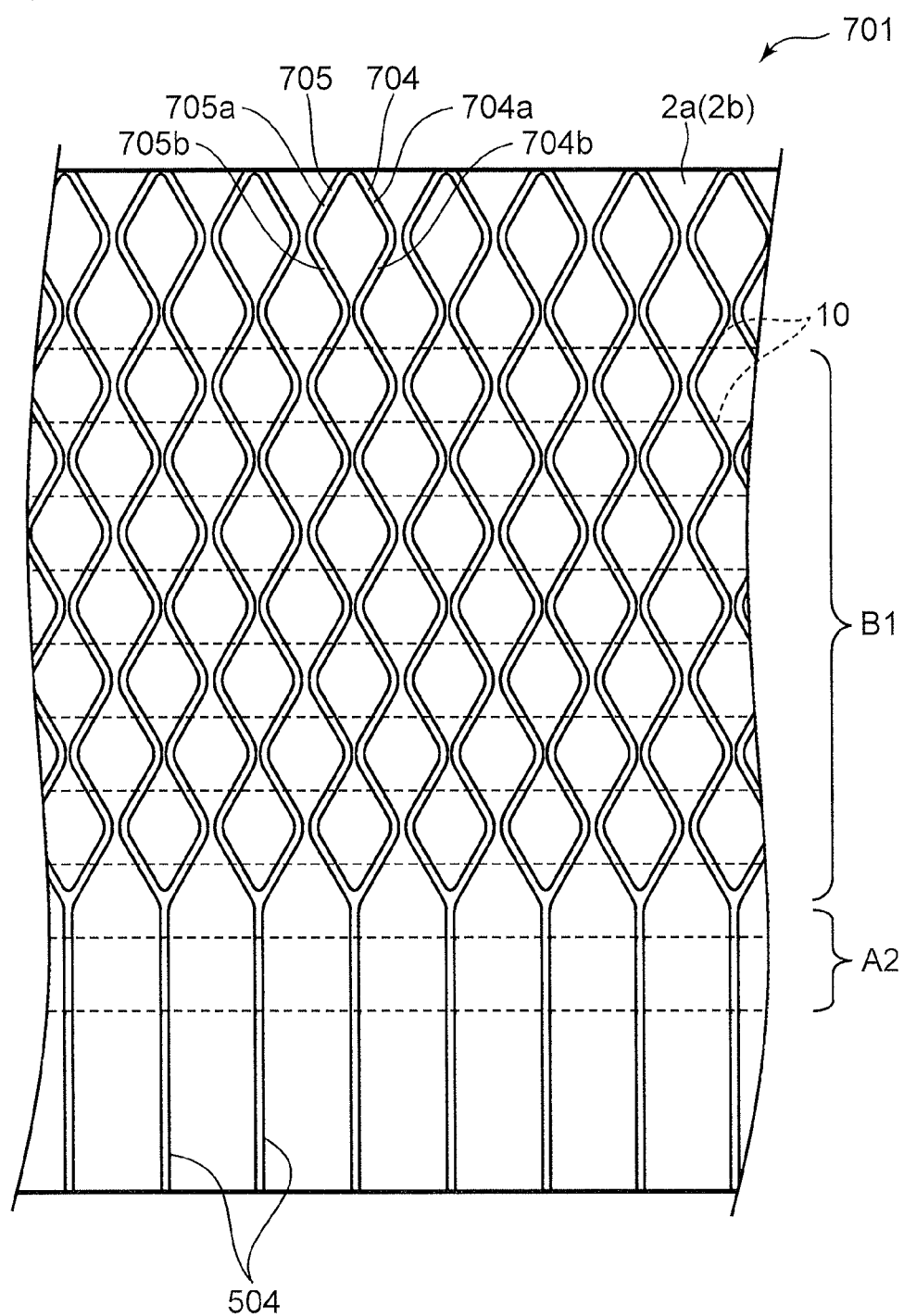
FIG. 20 is a plan view of a composite stretchable member according to yet still another embodiment of the present invention.

Further, the stretchable member may be configured as a stretchable member 701 depicted in FIG. 20.

In the example depicted in FIG. 20, a plurality of bonding sections 704 each extending along a zigzag line intersecting the longitudinal direction of the sheets 2a, 2b, i.e., a line extending in the width direction of the sheets 2a, 2b, while bending toward one side and the other side of the longitudinal direction of the sheets 2a, 2b plural times, are provided in a region B1 other than the straight pattern region A2, in place of the intersecting pattern region A1 in FIG. 19.

More specifically, in the example depicted in FIG. 20, in the region B1, the bonding sections 704 comprise: a plurality of first unit-bonding sections 704 lying side-by-side in the longitudinal direction of the sheets 2a, 2b in parallel relation to each other, and a plurality of second unit-bonding sections 705 located between adjacent ones of the first unit-bonding sections 704 and lying side-by-side in the longitudinal direction of the sheets 2a, 2b in parallel relation to each other. Each of the first unit-bonding sections 704 has a segment 704a extending rightwardly and obliquely downwardly, in FIG. 20, and a segment 704b extending from a lower end of the segment 704a leftwardly and obliquely downwardly, in FIG. 20, wherein the segment 704a and the segment 704b are arranged alternately and continuously in an upward-downward direction (the width direction of the sheets 2a, 2b). On the other hand, each of the second unit-bonding sections 705 is formed in a shape symmetrical to the first unit-bonding section 704, with respect to a line extending in the upward-downward direction, in FIG. 20 (a line extending in the width direction of the sheets 2a, 2b), and has a segment 705a opposed to the segment 704a of the first unit-bonding section 704 extending rightwardly and obliquely downwardly, and extending leftwardly and obliquely downwardly, in FIG. 20, and a segment 705b extending continuously from a lower end of the segment 705a rightwardly and obliquely downwardly, in FIG. 20.

Each of the elastic elements 10 extends in the longitudinal direction of the sheets 2a, 2b while passing through respective central areas of the segments 704a, 705a (704b, 705b) in the width direction of the sheets 2a, 2b.

In a boundary area between the region B1 and the straight pattern region A2, adjacent ones of the first unit-bonding sections 704 and the second unit-bonding sections 705 are joined together, and each of the bonding sections 504 forming the straight pattern linearly extends from the joined position along in the width direction of the sheets 2a, 2b.

When the bonding sections 705 is formed in the above manner, it becomes possible to keep down a ratio per unit area of the bonding sections to the region B1, as compared to the stretchable member depicted in FIG. 19. Specifically, in the example depicted in FIG. 19, the first bonding sections 4a and the second bonding sections 4b intersect each other, so that an area percentage per unit area of the bonding sections 4 (4c) in a vicinity of the intersection point becomes larger. Accordingly, in the vicinity of the intersection point, the composite stretchable member 601 becomes harder. Differently, in the example depicted in FIG. 20, the unit-bonding sections 704, 705 do not intersect each other, except the boundary area between the region B1 and the straight pattern region A2), so that it becomes possible to suppress an increase in area of bonding sections to be formed (area percentage per unit area of the bonding sections) so as to suppress hardening of the composite stretchable member 701 and provide good feel.

The elastic elements 10 may be arranged to have different spaced-apart distances between adjacent one thereof.

Further, as long as each of the elastic elements 10 extends along the longitudinal direction of the sheets 2a, 2b (the stretchable direction of the composite stretchable member 1), the elastic elements 10 may be arranged in non-parallel relation to extend in directions causing them to intersect each other, or may be arranged to extend in a certain direction while periodically or non-periodically meandering.

Further, one of the group of first bonding sections 4a and the group of second bonding sections 4b may be arranged to extend in the width direction of the sheets 2a, 2b.

Alternatively, one or each of the group of first bonding sections 4a and the group of second bonding sections 4b may be arranged to incline at an angle of 45 degree or more, with respect to the width direction of the sheets 2a, 2b (the direction orthogonal to the stretchable direction of the composite stretchable member 1).

Further, the intersection points 4c of the first bonding sections 4a with the second bonding sections 4b need not necessarily be arranged to lie side-by-side on a straight line extending in the width direction of the sheets 2a, 2b. For example, the intersection points 4c may be offset from each other in the longitudinal direction of the sheets 2a, 2b.

Further, the first elastic element-side intersection points 4d and the second elastic element-side intersection points 4e need not necessarily be arranged to lie in a straight line extending in the longitudinal direction of the sheets 2a, 2b. For example, the intersection points 4d, 4e may be offset from each other in the width direction of the sheets 2a, 2b.

Further, each of the elastic elements 10 may be disposed to pass through the intersection points of the first bonding sections 4a with the second bonding sections 4b (the bonding section-side intersection points 4c), and bonded to the sheets 2a, 2b at the points.

Further, the intersection points 4d of the elastic elements 10 with the first bonding sections 4a, and the intersection points 4e of the elastic elements 10 with the second bonding sections 4b, need not necessarily be arranged to lie in a straight line extending in the width direction of the sheets 2a, 2b. For example, the intersection points 4d, 4e may be offset from each other in the longitudinal direction of the sheets 2a, 2b.

Further, the intersection points 4d, 4e of the elastic elements 10 with the bonding sections 4 may be arranged at unequal intervals in the longitudinal direction of the sheets 2a, 2b.

The bonded structure of the elastic elements 10 and the sheets 2a, 2b are not limited to the above. That is, the rubber strings 10a in the elastic elements 10 may be bonded to the sheets 2a, 2b. For example, each of the elastic elements 10 may comprise a plurality of rubber strings 10a assembled as a bundle, wherein the sheets 2a, 2b may be welded to at least one of the rubber strings 10a located in an outer periphery of the elastic element 10. Even in this case, the sheets 2a, 2b are welded to the rubber strings 10a located in the outer periphery of the elastic element 10, so that it is possible to suppress damage to the remaining, non-bonded rubber strings 10a.

Further, each of the elastic elements 10 may be formed using silicone oil having a relatively low boiling point or the like, as the covering layer 10b. In this case, during welding of the elastic element 10 to the sheets 2a, 2b, after vaporizing the covering layer 10b, part of the rubber strings 10a may be directly bonded to the sheets 2a, 2b. In this case, the part of the rubber strings 10a and the sheets 2a, 2b may be bonded together, after melting at least one of them. Alternatively, as the rubber strings 10a, rubber strings having an adhesive force (cohesion) may be employed. In this case, the rubber strings 10a may be bonded to the sheets 2a, 2b by means of the adhesive force.

Further, the production method for the disposable diaper 20 using the composite stretchable member 1 is not limited to the above.

For example, the disposable diaper 20 may be produced in a process as depicted in FIG. 21.

Specifically, in this method, in a stage 1, one continuous body 201 of the composite stretchable member 1 extending in a conveyance direction is prepared, and conveyed in a longitudinal direction thereof. Further, a plurality of crotch portions 22 are arranged in a widthwise central region of the continuous body 201, in such a manner that a longitudinal direction of each of the crotch portions 22 is oriented orthogonal to the longitudinal direction of the continuous body 201. Then, the crotch portions 22 and the continuous body 201 are bonded together to form a bonded body 202 (bonded body forming step). In this method, a plurality of pairs of holes X each serving as leg openings for allowing legs of a wearer to be inserted therethrough are preliminarily formed in the continuous body 201, and then the crotch portions 22 are bonded to the continuous body 201. The formation of the holes X may be performed after bonding the crotch portions 22 to the continuous body 201.

Subsequently, in a stage 2, the bonded body 102 is double-folded along a folding line defined by a center line of the bonded body 102 in a width direction (a direction orthogonal to the longitudinal direction of the continuous body), in such a manner that each of the crotch portions 22 is located inward of the continuous body (double-folding step).

A stage 3 is the same as that in the above embodiment. That is, in the stage 3, superimposed portions of the continuous body 201 at an intermediate position between adjacent ones of the crotch portions 22 are bonded together along a direction orthogonal to the longitudinal direction of the continuous body 201, to thereby form a side seal (side sealing step), and the continuous body 201 is cut along a cutting line K in the side seal (cutting step).

As with the method in the above embodiment, this method makes it possible to produce a disposable diaper 20 capable of increasing a bonding force in a waist portion 20 thereof to suppressing breakage such as drop-off of the elastic elements 10.

In this method, there is no need to prepare and convey a plurality of continuous bodies of the composite stretchable member 1, so that it is possible to simplify a production apparatus. On the other hand, in the case where the disposable diaper 20 is produced using the pair of continuous bodies of the composite stretchable member 1 as in the above embodiment, it is possible to omit the formation of the holes serving as leg openings.

The aforementioned specific embodiments primarily include inventions having the following features.

According to a first aspect of the present invention, there is provided a composite stretchable member which is stretchable in a specific direction. The composite stretchable member comprises: two sheets which are opposed to each other; and a plurality of elastic elements each disposed between the sheets to extend along the specific direction in such a manner as to be stretchable in the specific direction, wherein: the sheets are bonded together in a plurality of bonding sections, wherein each of the bonding sections is configured to continuously extend along a line intersecting the specific direction and to intersect the plurality of elastic elements; and each of the elastic elements is bonded to the sheets at intersection points with the bonding sections.

In the composite stretchable member of the present invention, the sheets are continuously bonded together in the bonding sections, along a line intersecting the specific direction (a stretchable direction of the composite stretchable member), so that it becomes possible to increase a bonding force between the sheets. This makes it possible to prevent debonding between the sheets during use or the like. Further, each of the bonding sections continuously intersects the plurality of elastic elements, and each of the elastic elements is bonded to the sheets at these intersection points. Thus, as compared to the case where the bonding sections are intermittently provided, and arranged to intersect only part of the elastic elements, it becomes possible to ensure a larger number of bonded points of each of the elastic elements to the sheets so as to increase a bonding force between associated ones of the elastic elements and the sheets.

Preferably, in the composite stretchable member of the present invention, the bonding sections comprise: a plurality of first bonding sections extending parallel to each other along a first direction intersecting the specific direction; and a plurality of second bonding sections extending parallel to each other along a second direction intersecting the specific direction and the first direction, and each intersecting at least one of the first bonding sections.

According to this feature, the sheets are bonded together in the first and second bonding sections extending in different directions. Thus, even in a situation where an external force is applied to the composite stretchable member from different directions, it is possible to more reliably suppress debonding between the sheets or between associated ones of the sheets and the elastic elements. Further, the first bonding sections and the second bonding sections intersect each other, so that it is possible to increase a bonding force between the sheets in the vicinity of each of the intersection points between the first and second bonding sections, and thus a bonding force in the entire composite stretchable member.

Preferably, in the above composite stretchable member, each of the first direction and the second direction is a direction intersecting a direction orthogonal to the specific direction.

According to this feature, when an external force is applied to the specific direction, it is possible to reduce a normal component of the external force with respect to each of the bonding sections. This makes it possible to more reliably suppress debonding between the sheets in the bonding sections.

Preferably, in the above composite stretchable member, each of the first direction and the second direction is inclined at an angle of less than 45 degrees, with respect to the direction orthogonal to the specific direction.

According to this feature, it is possible to reduce a spaced-apart distance between the intersection points between the first bonding sections and the second bonding sections in the specific direction, i.e., the stretchable direction of the composite stretchable member. This makes it possible to more finely form gathers between the bonded points in the stretchable direction, in a non-stretched state of the composite stretchable member. Therefore, it is possible to provide a better feel.

Preferably, in the above composite stretchable member, intersection points of the first bonding sections with the second bonding sections lie in a straight line extending in the specific direction, and lie in a straight line extending in the direction orthogonal to the specific direction.

According to this feature, the intersection points between the first and second bonding sections can be arranged in an orderly manner, so that it is possible to form gathers between adjacent ones of the intersection points in a regular pattern so as to provide good appearance, and to increase a bonding force between the sheets in the specific direction and in a direction orthogonal to the specific direction.

Preferably, in the above composite stretchable member, each of the elastic elements intersects the first bonding sections and the second boding sections at points other than the intersection points of the first bonding sections with the second bonding sections.

According to this feature, each of the elastic elements is bonded to the sheets in the first bonding sections and the second boding sections, individually, so as to increase the number of bonded points of each of the elastic elements 10 to the sheets. This makes it possible to increase a bonding force between associated ones of the elastic elements and the sheets.

Preferably, in the above composite stretchable member, first elastic element-side intersection points which are intersection points of the elastic elements with the first bonding sections, and second elastic element-side intersection points which are intersection points of the elastic elements with the second bonding sections, lie in a straight line orthogonal to the specific direction.

According to this feature, it is possible to form gathers between adjacent ones of the bonded points of each of the elastic elements to the sheets, in such a manner as to lie side-by-side on a straight line extending in the direction orthogonal to the specific direction. This makes it possible to provide good appearance.

Preferably, in the above composite stretchable member, wherein intersection points of the first bonding sections with the second bonding sections lie in a straight line extending in the specific direction, and lie in a straight line extending in the direction orthogonal to the specific direction, each of the elastic elements intersects the first bonding sections and the second boding sections at points other than the intersection points of the first bonding sections with the second bonding sections, and intersect the first and second bonding sections at equal intervals in the specific direction.

According to this feature, it becomes possible to uniform, in the specific direction, sizes of gathers formed between adjacent ones of the bonded points of each of the elastic elements to the sheets (dimensions of the gathers protruding outwardly), while increasing a bonding force between the sheets and a bonding force between associated ones of the elastic elements and the sheets, thereby providing good appearance and good feel.

Preferably, in the above composite stretchable member, each of the sheets includes: an intersecting pattern region in which the bonding sections comprise the plurality of first bonding sections and the plurality of second bonding sections; and a straight pattern region which is located next to the intersecting pattern region and in which the bonding sections comprise a plurality of third bonding sections each extending from a respective one of part of intersection points of the first bonding sections with the second bonding sections, in a direction orthogonal to the specific direction.

According to this feature, it becomes possible to further increase a bonding force between the sheets in the specific direction in the straight pattern region, while increasing a bonding force between the sheets in a direction intersecting the specific direction in the intersecting pattern region.

Further, when this composite stretchable member is applied to a waist portion of a wearable article, gathers formed in the intersecting pattern region can provide good appearance and good feel, and gathers formed in the straight pattern region can form open spaces opened outwardly from the edge of the waist portion to provide good breathability.

Differently from the above arrangement, each of the bonding sections may be disposed to extend in a direction orthogonal to the specific direction.

According to this feature, it becomes possible to increase a bonding force between the sheets in the direction orthogonal to the specific direction.

Preferably, in the above composite stretchable member, each of the elastic elements comprises a plurality of fiber-shaped elastic bodies assembled as a bundle, wherein a peripheral surface of each of at least part of the plurality of fiber-shaped elastic bodies is covered by a covering layer, and the elastic element and each of the sheets are bonded together by means of welding of the covering layer to the sheet.

According to this feature, it becomes possible to suppress breakage or the like of the fiber-shaped elastic elements which would otherwise occur when the elastic elements are clamped and pressed during bonding.

Alternatively, each of the elastic elements may comprise a plurality of fiber-shaped elastic bodies assembled as a bundle, wherein the elastic element and each of the sheets are bonded together by means of welding of the sheet to at least one of the fiber-shaped elastic bodies located in a periphery of the elastic element.

In this case, it also becomes possible to suppress breakage or the like of the fiber-shaped elastic elements which would otherwise occur when the elastic elements are clamped and pressed during bonding.

According to a second aspect of the present invention, there is provided a wearable article comprising a waist portion to be disposed around a waist region of a wearer, wherein at least part of the waist portion is formed of the above composite stretchable member.

The composite stretchable member according to the first aspect of the present invention is capable of increase respective bonding forces between the sheets and between associated ones of the elastic elements and the sheets, as mentioned above. Thus, by using this composite stretchable member in at least part of the waist portion of the wearable article, it becomes possible to ensure stretchability to provide wearing comfort, while suppressing breakage such as drop-off of the elastic elements in the waist portion during attaching and removing of the wearable article.

According to a third aspect of the present invention, there is provided a method of producing a wearable article, wherein the wearable article comprises a waist portion to be disposed around a waist region of a wearer, and a crotch portion to be disposed in a crotch region of the wearer. The method comprises: a bonded body forming step of, after providing a continuous body of the above composite stretchable member, conveying the continuous body in a longitudinal direction thereof so as to form the waist portion, and bonding the crotch portion to the continuous body, such that a longitudinal direction of the crotch portion is oriented orthogonal to the longitudinal direction of the continuous body to thereby form a bonded body; a double-folding step of double-folding the bonded body along a folding line defined by a center line of the bonded body in a width direction orthogonal to the longitudinal direction of the continuous body; a side sealing step of mutually bonding superimposed portions of the continuous body at an intermediate position between adjacent ones of a series of the crotch portions in the longitudinal direction of the continuous body, along a direction orthogonal to the longitudinal direction of the continuous body, to thereby form a side seal; and a cutting step of cutting the continuous body along a cutting line in the side seal.

In the method according to the third aspect of the present invention, the waist portion can be formed using the composite stretchable member having a high bonding force as mentioned above.

Then, the bonded body formed by bonding the crotch portions and the continuous body of the composite stretchable member together is double-folded, and, after forming the side seal in the bonded body, the resulting bonded body is cut to produce the wearable article.

Thus, the method according to the third aspect of the present invention makes it possible to produce a wearable article comprising a waist portion having a high bonding force and capable of suppressing breakage such as drop-off of the elastic elements during attaching and removing of the wearable article.

Preferably, in the method of the present invention, the bonded body forming step includes, after providing a pair of the continuous bodies of the composite stretchable member, conveying the pair of continuous bodies parallel to each other; and bonding the crotch portion so as to straddle the pair of continuous bodies, to thereby form the bonded body.

According to this feature, there is no need to form holes serving as leg openings for allowing legs to be inserted therethrough, so that it is possible to more easily produce a wearable article which is less likely to undergo breakage.

The invention claimed is:

1. A composite stretchable member which is stretchable in a specific direction, comprising:
   two sheets which are opposed to each other; and
   a plurality of elastic elements each disposed between the sheets to extend along the specific direction in such a manner as to be stretchable in the specific direction, wherein:
   the sheets are bonded together in a plurality of bonding sections, each of the bonding sections being configured to continuously extend along a line intersecting the specific direction and to intersect the plurality of elastic elements; and
   each of the elastic elements is bonded to the sheets at intersection points with the bonding sections.

2. The composite stretchable member according to claim 1, wherein the bonding sections comprise:
   a plurality of first bonding sections extending parallel to each other along a first direction intersecting the specific direction; and
   a plurality of second bonding sections extending parallel to each other along a second direction intersecting the specific direction and the first direction, and each intersecting at least one of the first bonding sections.

3. The composite stretchable member according to claim 2, wherein each of the first direction and the second direction is a direction intersecting a direction orthogonal to the specific direction.

4. The composite stretchable member according to claim 3, wherein each of the first direction and the second direction is inclined at an angle of less than 45 degrees, with respect to the direction orthogonal to the specific direction.

5. The composite stretchable member according to claim 4, wherein intersection points of the first bonding sections with the second bonding sections lie in a straight line extending in the specific direction, and lie in a straight line extending in the direction orthogonal to the specific direction.

6. The composite stretchable member according to claim 2, wherein each of the elastic elements intersects the first bonding sections and the second bonding sections at points other than the intersection points of the first bonding sections with the second bonding sections.

7. The composite stretchable member according to claim 2, wherein first elastic element-side intersection points which are intersection points of the elastic elements with the first bonding sections, and second elastic element-side intersection points which are intersection points of the elastic elements with the second bonding sections, lie in a straight line orthogonal to the specific direction.

8. The composite stretchable member according to claim 5, wherein each of the elastic elements intersects the first bonding sections and the second bonding sections at points other than the intersection points of the first bonding sections with the second bonding sections, and intersect the first and second bonding sections at equal intervals in the specific direction.

9. The composite stretchable member according to claim 2, wherein each of the sheets includes:
   an intersecting pattern region in which the bonding sections comprise the plurality of first bonding sections and the plurality of second bonding sections; and
   a straight pattern region which is located next to the intersecting pattern region and in which the bonding sections comprise a plurality of third bonding sections each extending from a respective one of part of intersection points of the first bonding sections with the second bonding sections, in a direction orthogonal to the specific direction.

10. The composite stretchable member according to claim 1, wherein each of the bonding sections extends in a direction orthogonal to the specific direction.

11. The composite stretchable member according to claim 1, wherein each of the elastic elements comprises a plurality of fiber-shaped elastic bodies assembled as a bundle, and wherein a peripheral surface of each of at least part of the plurality of fiber-shaped elastic bodies is covered by a covering layer, and the elastic element and each of the sheets are bonded together by welding of the covering layer to the sheet.

12. The composite stretchable member according to claim 1, wherein each of the elastic elements comprises a plurality of fiber-shaped elastic bodies assembled as a bundle, and wherein the elastic element and each of the sheets are bonded together by welding of the sheet to at least one of the fiber-shaped elastic bodies located in a periphery of the elastic element.

13. A wearable article comprising a waist portion to be disposed around a waist region of a wearer, wherein at least part of the waist portion is formed of the composite stretchable member according to claim 1.

14. A method of producing a wearable article, the wearable article comprising a waist portion to be disposed around a waist region of a wearer and a crotch portion to be disposed in a crotch region of the wearer, the method comprising:
   a bonded body forming step of, after providing a continuous body of the composite stretchable member according to claim 1, conveying the continuous body in a longitudinal direction thereof so as to form the waist portion, and bonding the crotch portion to the continuous body, such that a longitudinal direction of the crotch portion is oriented orthogonal to the longitudinal direction of the continuous body to thereby form a bonded body;

a double-folding step of double-folding the bonded body along a folding line defined by a center line of the bonded body in a width direction orthogonal to the longitudinal direction of the continuous body;

a side sealing step of mutually bonding superimposed portions of the continuous body at an intermediate position between adjacent ones of a series of the crotch portions in the longitudinal direction of the continuous body, along a direction orthogonal to the longitudinal direction of the continuous body, to thereby form a side seal; and a cutting step of cutting the continuous body along a cutting line in the side seal.

15. The method according to claim 14, wherein the bonded body forming step includes, after providing a pair of the continuous bodies of the composite stretchable member, conveying the pair of continuous bodies parallel to each other; and bonding the crotch portion so as to straddle the pair of continuous bodies, to thereby form the bonded body.

* * * * *